(12) United States Patent
Shimohara et al.

(10) Patent No.: US 8,173,226 B2
(45) Date of Patent: May 8, 2012

(54) POLYMERIZABLE COMPOUND, POLYMER, INK COMPOSITION, PRINTED ARTICLES AND INKJET RECORDING METHOD

(75) Inventors: Norihide Shimohara, Kanagawa (JP); Hisato Nagase, Kanagawa (JP); Shigetomo Tsujihata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 620 days.

(21) Appl. No.: 12/052,047

(22) Filed: Mar. 20, 2008

(65) Prior Publication Data

US 2008/0241416 A1 Oct. 2, 2008

(30) Foreign Application Priority Data

Mar. 30, 2007 (JP) ................................. 2007-095456
Nov. 13, 2007 (JP) ................................. 2007-294571

(51) Int. Cl.
*C08J 7/04* (2006.01)

(52) U.S. Cl. ..... 427/511; 427/508; 427/510; 106/31.13; 106/31.6; 106/31.85

(58) Field of Classification Search .................. 427/508, 427/510; 106/31.13, 31.6, 31.85
See application file for complete search history.

(56) References Cited

U.S. PATENT DOCUMENTS

| | | | |
|---|---|---|---|
| 5,466,807 A | 11/1995 | Dietz | |
| 2003/0231234 A1* | 12/2003 | Ushirogouchi et al. | 347/100 |
| 2004/0016370 A1 | 1/2004 | Olson | |
| 2006/0023043 A1* | 2/2006 | Ishibashi et al. | 347/100 |

FOREIGN PATENT DOCUMENTS

| | | |
|---|---|---|
| EP | 2058375 A2 | 5/2009 |
| EP | 2093265 A1 | 8/2009 |
| JP | 2001-167885 * | 6/2001 |
| JP | 2003-119414 A | 4/2003 |
| JP | 2003-321628 A | 11/2003 |
| JP | 2004-018656 A | 1/2004 |
| JP | 2004-131589 A | 4/2004 |
| WO | 91/02032 A1 | 2/1991 |
| WO | 2004/029028 A2 | 4/2004 |
| WO | 2005/102250 A1 | 11/2005 |
| WO | WO2006/005823 * | 1/2006 |

OTHER PUBLICATIONS

Tian et al. "Positive and Negative Fluorescent Imaging Induced by Naphthalimide Polymers" Journal of Materials Chemistry (2002) 1262-1267.*
Dominik Woll et al. "Radical Polymerization Tracked by Single Molecule Spectroscopy" Angew. Chem. Int. Ed., vol. 47, Jan. 11, 2008, pp. 783-787.
Database Beilstein, Beilstein Institute for Organic Chemistry, Frankfurt-Main, DE; XP002487960 Database Accession No. BRN: 10195975 Australian Journal of Chemistry, vol. 57, No. 9, 2004, pp. 885-894.
Database Beilstein, Beilstein Institute for Organic Chemistry, Frankfurt-Main, DE; XP002487961 Database Accession No. BRN: 9232054 Journal of Materials Chemistry, vol. 12, No. 5, 2002, pp. 1262-1267.
Database Beilstein, Beilstein Institute for Organic Chemistry, Frankfurt-Main, DE; XP002487962 Database Accession No. BRN: 1490580 Yuki Gosei Kagaku Kyokaishi, vol. 30, 1972, p. 897.
Database Beilstein, Beilstein Institute for Organic Chemistry, Frankfurt-Main, DE; XP002487963 Database Accession No. BRN: 8965407 Journal of Chemical Physics, vol. 114, No. 5, 2001, pp. 6739-6743.
European Official Communication dated Mar. 8, 2012 in EP Application No. 08 005 793.8.

* cited by examiner

*Primary Examiner* — Robert S Walters, Jr.
(74) *Attorney, Agent, or Firm* — Sughrue Mion, PLLC

(57) ABSTRACT

A polymerizable compound represented by the following formula (1):

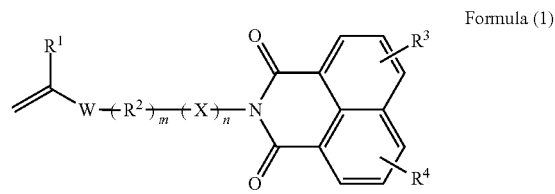

wherein, in the formula (1), $R^1$ represents any one of a hydrogen atom, a substituted alkyl group, and an unsubstituted alkyl group; $R^2$ represents an alkylene group; W represents any one of —CO—, —C(=O)O—, —CONH—, —OC(=O)—, and a phenylene group; X represents any one of —CO—, —NHCO—, —OC(=O)—, —CH(OH)CH$_2$—, and —SO$_2$—; $R^3$ and $R^4$ represent a monovalent substituent; $R^3$ and $R^4$ may be bound to each other to form a ring structure; and m and n each independently represent 0 or 1.

8 Claims, No Drawings

POLYMERIZABLE COMPOUND, POLYMER, INK COMPOSITION, PRINTED ARTICLES AND INKJET RECORDING METHOD

BACKGROUND OF THE INVENTION

1. Field of the Invention

The present invention relates to a polymerizable compound and a polymer. In particular, the present invention relates to a novel polymerizable compound that is very useful industrially, and a polymer that comprises a copolymer unit derived from the polymerizable compound and is used as a pigment dispersant to be used for color filters, inkjet ink, etc. The present invention also relates to an ink composition suitably used for inkjet recording, a printed article using the ink composition, and an inkjet recording method using the ink composition. In particular, the present invention relates to: an ink composition suitable for inkjet recording, the ink composition being superior in the dispersibility of a colorant so that it has excellent coloring property, being cured by irradiation with an active radiation ray without generating volatile components and enabling the formation of a high quality image; a printed article obtained using the ink composition, and an inkjet recording method using the ink composition.

2. Description of the Related Art

As an image recording method for forming an image on a recording medium such as paper based on image data signals, there are an electrophotographic system, sublimation-type and melt-type thermal transfer systems, an inkjet system, etc. In particular, the inkjet system is applicable to an inexpensive apparatus, and performs direct image formation on a recording medium by ejecting ink only to image areas where ink deposition is necessary; therefore, the inkjet system uses ink effectively, thus reducing the running cost. Further, the inkjet system generates less noise and is a superior image recording system.

The inkjet system enables printing on recording media that do not absorb water, such as plastic sheets and metallic plates, as well as on paper. In the inkjet system, it is an important target to achieve higher printing speed and higher printing quality, and the time that liquid droplets take to dry and cure after printing has significant influence on the sharpness of the image. In one inkjet system, an inkjet recording ink that can be cured by irradiation with an active radiation ray is used. According to this system, sharp images can be formed by curing ink droplets by irradiation with an active radiation ray immediately after printing.

In order to form highly accurate images with excellent coloring properties, the curable ink composition in such an inkjet recording ink that can be cured is required to have high dispersibility of a pigment, and stability over time. Reduction in the pigment size is necessary for imparting clear tone and high tinting strength to the ink composition. In particular, ejected droplets of the inkjet ink exert a significant influence on the sharpness of images; therefore, the ejection quantity of the ink droplets needs to be small, and the size of the pigment particles contained in the ink has to be smaller than the thickness of the film formed by curing of the ink. However, when the size of the pigment particles is reduced so as to achieve higher tinting strength, the pigment particles are hard to disperse, and pigment aggregates are easily formed. Another problem is created in that the viscosity of the ink composition is increased by the addition of a dispersant. The formation of the pigment aggregates and the increase in the viscosity of the ink composition both adversely affect ink ejection property, and such an ink composition is not preferred.

When an ink composition is used in inkjet recording, the ink composition is contained in a cartridge. The ink composition in the cartridge is heated at ejection and cooled at a non-ejection time and at storage; in this way, the ink composition undergoes repeated temperature changes (heating-cooling). This temperature changes also adversely affect the pigment dispersibility, and the pigment dispersibility is deteriorated with time, causing problems that pigment aggregates are easily formed, or the increase in the viscosity of the ink composition easily occurs.

Accordingly, there is a demand for an ink composition having sufficient fluidity and excellent stability of the pigment dispersion over time, in which fine colorant particles are dispersed stably. Various proposals have been made concerning dispersants for achieving stable pigment dispersion liquids.

In order to improve compatibility with the pigment, an ink composition using a pigment derivative as a dispersant (see, for example, Japanese Patent Application Laid-pen (JP-A) Nos. 2003-119414 and 2004-18656); an ink composition that uses a polymer having a basic group as a dispersant for a specific pigment such as a phthalocyanine-based or quinacridone-based pigment (see, for example, JP-A No. 2003-321628); and an ink composition which is free of organic solvent and contains a dispersant such as poly(ethyleneimine)-poly(12-hydroxystearic acid) graft polymer and a specific monomer that dissolves the dispersant (see, for example, JP-A No. 2004-131589) have been proposed.

In these ink compositions, the dispersion stability of pigments is actually improved owing to the function of the dispersant. However, the size of the pigment used in the ink composition is not sufficiently small, and there is a room for improvement of dispersibility of finer pigment particles. Further, the ink composition also has a problem in that the dispersion stability upon long-term storage or upon repeated temperature changes is still insufficient.

BRIEF SUMMARY OF THE INVENTION

An object of the present invention is to solve the conventional problems and to achieve the following objects. Specifically, an object of the present invention is to provide (1) a novel polymerizable compound that is very useful industrially, (2) a polymer that includes a copolymer unit derived from the polymerizable compound and is used as a pigment dispersant which improves the dispersibility of a fine pigment and stability thereof, (3) an ink composition suitable for inkjet recording, which can form a high quality image with clear tone and high tinting strength and can be cured by irradiation with an active radiation ray without generating volatile components, (4) a printed article obtained using the ink composition, and (5) an inkjet recording method using the ink composition.

As a result of dedicated investigations conducted by the present inventors, they have found a polymerizable compound having a specific nitrogen-containing heterocyclic structure, and have found that use of the polymer that includes a copolymer unit derived from the polymerizable compound (monomer) as a pigment dispersant can solve the problems, and thus the present invention has been made.

Means for solving the above-mentioned problems are as follows. Specifically,

<1> A polymerizable compound represented by the following formula (1):

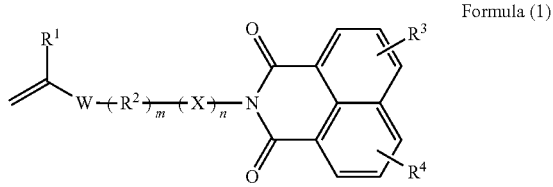

Formula (1)

wherein, in the formula (1), R¹ represents any one of a hydrogen atom, a substituted alkyl group, and an unsubstituted alkyl group; R² represents an alkylene group; W represents any one of —CO—, —C(=O)O—, —CONH—, —OC(=O)—, and a phenylene group; X represents any one of —CO—, —NHCO—, —OC(=O)—, —CH(OH)CH₂—, and —SO₂—; R³ and R⁴ represent a monovalent substituent; R³ and R⁴ may be bound to each other to form a ring structure; and m and n each independently represent 0 or 1.

<2> The polymerizable compound according to the <1>, which is represented by the following formula (2):

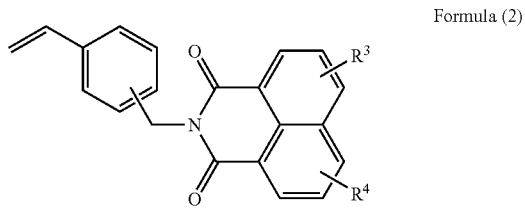

Formula (2)

wherein, in the formula (2), R³ and R⁴ represent a monovalent substituent; and R³ and R⁴ may be bound to each other to form a ring structure.

<3> A polymer including a copolymer unit derived from a monomer represented by formula (1).

<4> The polymer according to the <3>, further including a copolymer unit derived from a monomer represented by formula (2).

<5> The polymer according to one of the <3> and <4>, wherein the polymer is a graft copolymer containing, as a copolymer unit, a polymerizable oligomer (macromonomer) having an ethylenically unsaturated double bond at a terminal thereof.

<6> An ink composition including: the polymer of any one of the <3> to <5>; a polymerizable compound (a); and a pigment (b).

<7> The ink composition according to the <6>, further including a polymerization initiator (c).

<8> The ink composition according to the <7>, wherein the polymerizable compound (a) is a radical polymerizable compound, and the polymerization initiator (c) is a photo-radical generator.

<9> The ink composition according to the <7>, wherein the polymerizable compound (a) is a cationic polymerizable compound, and the polymerization initiator (c) is a photo-acid generator.

<10> The ink composition according to any one of the <6> to <9>, which is used for inkjet recording.

<11> A printed article obtained by curing the ink composition of any one of the <6> to <10>.

<12> An inkjet recording method including: ejecting the ink composition of any one of the <6> to <10> on a recording medium using an inkjet printer; and irradiating the ink composition ejected with an active radiation ray to cure the ink composition.

The present invention can solve the conventional problems and can achieve the above object. By using a high-molecular compound that gives excellent dispersibility and dispersion stability, the present invention can provide an ink composition suitable for inkjet recording which is superior in the dispersibility of fine pigments and in the stability of the dispersion, enables the formation of a high quality image having a sharp color tone and high tinting strength, and can be cured by irradiation with an active radiation ray.

In addition, the present invention can provide a printed article with a high quality image which was obtained using the ink composition that can be cured by irradiation with an active radiation ray and provide a sharp color tone and high tinting strength.

DETAILED DESCRIPTION OF THE INVENTION

The present invention will be described in detail below.
(Polymerizable Compound)

The polymerizable compound of the present invention is represented by the following formula (1).

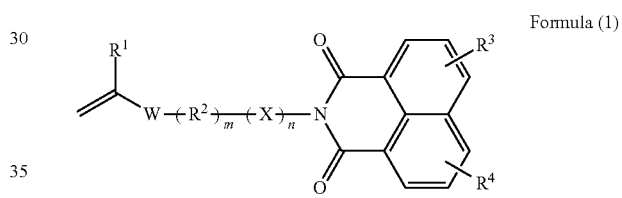

Formula (1)

<R¹ in Formula (1)>

In the formula (1), R¹ represents a hydrogen atom, or a substituted or unsubstituted alkyl group. The alkyl group has preferably 1 to 12 carbon atoms, more preferably 1 to 8 carbon atoms, still more preferably 1 to 4 carbon atoms. Examples of the alkyl group include a methyl group, an ethyl group, a propyl group, an n-butyl group, an i-butyl group, a t-butyl group, an n-hexyl group, a cyclohexyl group, a 2-hydroxyethyl group, a 3-hydroxypropyl group, a 2-hydroxypropyl group, and a 2-methoxyethyl group.

<R² in Formula (1)>

R² represents an alkylene group and has preferably 1 to 12 carbon atoms, more preferably 1 to 8 carbon atoms, still more preferably 1 to 4 carbon atoms. Examples of the alkylene group include a methylene group, an ethylene group, a propylene group, a trimethylene group, and a tetramethylene group.

<W in Formula (1)>

W represents —CO—, —C(=O)O—, —CONH—, —OC(=O)—, or a phenylene group.

<X in Formula (1)>

X represents —CO—, —NHCO—, —OC(=O)—, —CH(OH)CH₂—, or —SO₂.

<m and n in Formula (1)> m and n each independently represent 0 or 1.

<R³ and R⁴ in Formula (1)>

R³ and R⁴ represent a monovalent substituent. R³ and R⁴ may be bound to each other to form a ring structure.

The monovalent substituent for R³ or R⁴ is preferably an alkyl group, an aryl group, a halogen atom, an alkoxy group, an aryloxy group, an alkylthio group, an arylthio group, an alkoxycarbonyl group, an acylamino group, a carbamoyl group, a cyano group, an alkylsulfonyl group, an arylsulfonyl group, an acyl group, or a sulfamoyl group, and more preferably, a halogen atom, an alkyl group, an aryl group, an alkoxy group, an aryloxy group, an alkylthio group, an arylthio group, an acylamino group, or a sulfonylamino group.

The substituent represented by $R^3$ or $R^4$ may be unsubstituted or substituted. For the substituent that can be introduced into the substituent, an alkyl group, an aryl group, a halogen atom, an alkoxy group, an aryloxy group, an alkoxycarbonyl group, an acyloxy group, an acylamino group, a carbamoyl group, a cyano group, a carboxyl group, a sulfonyl group, and a heterocyclic residue are preferable.

The alkyl group for $R^3$ or $R^4$ is preferably an alkyl group having 1 to 30 total carbon atoms, more preferably, an alkyl group having 1 to 20 total carbon atoms. Specifically, a methyl group, an ethyl group, a butyl group, a hexyl group, an octyl group, a 2-ethylhexyl group, a 3,5,5-trimethylhexyl group, a dodecyl group, an octadecyl group, a benzyl group, a (4-ethoxyphenyl)methyl group, an N,N-diethyl carbamoyl methyl group, an N,N-dibutyl carbamoyl methyl group, a 1-(N,N-dibutyl carbamoyl)ethyl group, a 2-methoxy ethyl group, a 1-methyl-2-phenoxyethyl group, a (4-chlorophenyl)methyl group and a (2,4-dichlorophenyl)methyl group are preferable, and an ethyl group, a butyl group, a hexyl group, a benzyl group, an N,N-diethyl carbamoyl methyl group, an N,N-dibutyl carbamoyl methyl group, a 1-(N,N-dibutyl carbamoyl)ethyl group, a 1-methyl-2-phenoxyethyl group, a (4-chlorophenyl)methyl group and a (2,4-dichlorophenyl)methyl group are more preferable.

The aryl group for $R^3$ or $R^4$ is preferably an aryl group having 6 to 30 total carbon atoms, more preferably, an aryl group having 1 to 20 total carbon atoms. Specifically, a phenyl group, a 2-methylphenyl group, a 3-methylphenyl group, a 4-methylphenyl group, a 4-phenylphenoxy group, a 4-chlorophenyl group, a 2-methoxyphenyl group, a 3-ethoxyphenyl group, a 4-butoxyphenyl group, a 2,4-diethoxyphenyl group, a 2,5-dibutoxyphenyl group, a 4-phenoxyphenyl group, a naphthyl group, a 4-dibutyl carbamoyl phenyl group and a 4-dibutyl sulfamoyl phenyl group are preferable, and a phenyl group, a 2-methylphenyl group, a 3-methylphenyl group, a 4-methylphenyl group, a 4-chlorophenyl group, a 2-methoxyphenyl group, a 3-ethoxyphenyl group and a 4-butoxyphenyl group are more preferable.

The halogen atom for $R^3$ or $R^4$ is preferably a fluorine atom, a chlorine atom, a bromine atom or an iodine atom, and more preferably a fluorine atom or a chlorine atom.

The alkoxy group for $R^3$ or $R^4$ is preferably an alkoxy group having 1 to 30 total carbon atoms, more preferably, an alkoxy group having 1 to 20 total carbon atoms. For the substituent, a methoxy group, an ethoxy group, a propoxy group, a butoxy group, a hexyloxy group, a 2-ethylhexyloxy group, a 3,5,5-trimethyl hexyloxy group, an octyloxy group, a decyloxy group, a 2-phenoxyethoxy group, a 2-(3,5-di-t-butylphenoxy)ethoxy group, a dibutyl carbamoyl methoxy group, a hexadecyloxy group and an octadecyloxy group are preferable, and a methoxy group, an ethoxy group, a butoxy group, a hexyloxy group, a 2-ethyl hexyloxy group, a 3,5,5-trimethyl hexyloxy group, a 2-phenoxyethoxy group and a dibutyl carbamoyl methoxy group are more preferable.

The aryloxy group for $R^3$ or $R^4$ is preferably an aryloxy group having 6 to 30 total carbon atoms, more preferably, an aryloxy group having 6 to 20 total carbon atoms. For the substituent, a phenoxy group, a tolyloxy group, a 4-chlorophenyloxy group, a 4-acetamide phenyloxy group, a 2-butoxyphenyloxy group, a 2-benzoyl aminophenyloxy group, a 2,5-dimethoxy-4-nitrophenyloxy group and a 3-octyloxy phenyloxy group are preferable, and a phenoxy group, a tolyloxy group, a 4-chlorophenyloxy group, a 4-acetamide phenyloxy group, a 2-butoxyphenyloxy group and a 2,5-dimethoxy-4-nitrophenyloxy group are more preferable.

The alkylthio group for $R^3$ or $R^4$ is preferably an alkylthio group having 1 to 30 total carbon atoms, more preferably, an alkylthio group having 1 to 20 total carbon atoms. For the substituent, a methylthio group, an ethylthio group, a butylthio group, a hexylthio group, a 2-ethylhexylthio group, a 3,5,5-trimethylhexylthio group, an octylthio group, a decylthio group, a 2-phenoxyethylthio group, a 2-(3,5-di-t-butylphenoxy)ethylthio group, a dibutyl carbamoyl methylthio group, a hexadecylthio group and an octadecylthio group are preferable, and a methylthio group, an ethylthio group, a butylthio group, a hexylthio group, a 2-ethylhexylthio group, a 3,5,5-trimethylhexylthio group, a 2-phenoxyethylthio group and a dibutyl carbamoyl methylthio group are more preferable.

The arylthio group for $R^3$ or $R^4$ is preferably an arylthio group having 6 to 30 total carbon atoms, more preferably, an arylthio group having 6 to 20 total carbon atoms. For the substituent, a phenylthio group, a tolylthio group, a 4-chlorophenylthio group, a 4-acetamide phenylthio group, a 2-butoxyphenylthio group, a 2-benzoyl aminophenylthio group, a 2,5-dimethoxy-4-nitrophenylthio group, a 3-octyloxy phenylthio group are preferable, and a phenylthio group, a tolylthio group, a 4-chlorophenylthio group, a 4-acetamide phenylthio group, a 2-butoxyphenylthio group and a 2,5-dimethoxy-4-nitrophenylthio group are more preferable.

The alkoxycarbonyl group for $R^3$ or $R^4$ is preferably an alkoxycarbonyl group having 2 to 30 total carbon atoms, more preferably, an alkoxycarbonyl group having 2 to 20 total carbon atoms. For the substituent, a methoxycarbonyl group, an ethoxycarbonyl group, a butoxycarbonyl group, a phenoxycarbonyl group, a (2-ethylhexyl) oxycarbonyl group, a hexyloxycarbonyl group, an octyloxycarbonyl group, a (4-methoxyphenyl) oxycarbonyl group are preferable, and a methoxycarbonyl group, an ethoxycarbonyl group, a butoxycarbonyl group and a phenoxycarbonyl group are more preferable.

The acylamino group for $R^3$ or $R^4$ is preferably an acylamino group having 1 to 30 total carbon atoms, more preferably, an acylamino group having 1 to 20 total carbon atoms. For the substituent, a formylamino group, an acetylamino group, a butyrylamino group, a lauroylamino group, a benzoylamino group, a toluoylamino group, a phenoxyacetyl group, a (4-methoxyphenoxy)acetyl group, a 2',4'-dichlorobenzoylamino group, a 2',4'-di-t-amylbenzoylamino group, an acetylmethylamino group, a benzoylmethylamino group and an acetylbenzylamino group are preferable, and an acetylamino group, a butyrylamino group, a benzoylamino group, a toluoylamino group, a phenoxyacetyl group, a 2',4'-di-t-amylbenzoylamino group, an acetylmethylamino group, a benzoylmethylamino group and an acetylbenzylamino group are more preferable.

The carbamoyl group for $R^3$ or $R^4$ is preferably a carbamoyl group having 1 to 30 total carbon atoms, more preferably, a carbamoyl group having 1 to 20 total carbon atoms. For the substituent, a carbamoyl group, an N-phenylcarbamoyl group, an N-butylcarbamoyl group, an N-octylcarbamoyl group, an N,N-dimethylcarbamoyl group, an N,N-diethylcarbamoyl group, an N,N-dibutylcarbamoyl group, an N,N-dihexylcarbamoyl group, an N,N-diphenylcarbamoyl group, an N-methyl-N-phenylcarbamoyl group, an N-ethyl-N-phenylcarbamoyl group, an N-methyl-N-tolylcarbamoyl group, a morpholinocarbonyl group, a piperidinocarbonyl group and an N,N-bis(2-methoxyethyl)carbamoyl group are preferable, and an N-butylcarbamoyl group, an N-octylcarbamoyl group, an N-phenylcarbamoyl group, an N,N-diethylcarbamoyl group, an N,N-dibutylcarbamoyl group and an N-methyl-N-phenylcarbamoyl group are more preferable.

The alkylsulfonyl group for $R^3$ or $R^4$ is preferably an alkylsulfonyl group having 1 to 30 total carbon atoms, more preferably, an alkylsulfonyl group having 1 to 20 total carbon atoms. For the substituent, a methylsulfonyl group, an ethylsulfonyl group, a butylsulfonyl group, a hexylsulfonyl group and a benzylsulfonyl group are preferable, and a methylsulfonyl group and a benzylsulfonyl group are more preferable.

The arylsulfonyl group for $R^3$ or $R^4$ is preferably an arylsulfonyl group having 1 to 30 total carbon atoms, more preferably, an arylsulfonyl group having 1 to 20 total carbon atoms. For the substituent, a phenylsulfonyl group, a 4-methylphenylsulfonyl group, a naphthylsulfonyl group, a 4-methoxysulfonyl group and a 4-chlorophenyl sulfonyl group are preferable, and a methyl sulfonyl group, a phenyl sulfonyl group and a 4-methylphenyl sulfonyl group are more preferable.

The acyl group for $R^3$ or $R^4$ is preferably an acyl group having 1 to 30 total carbon atoms, more preferably, an acyl group having 1 to 20 total carbon atoms. For the substituent, a formyl group, an acetyl group, a propionyl group, a pivaloyl group, a butyloyl group, a 4-phenoxy butyloyl group, a benzoyl group, a (4-ethoxyphenyl) carbonyl group, a (2-buthoxyphenyl) carbonyl group and a (4-chlorophenyl) carbonyl group are preferable, and a formyl group, an acetyl group, a propionyl group, a pivaloyl group, a benzoyl group and a (4-chlorophenyl) carbonyl group are more preferable.

The sulfamoyl group for $R^3$ or $R^4$ is preferably a sulfamoyl group having 1 to 30 total carbon atoms, more preferably, a sulfamoyl group having 1 to 20 total carbon atoms. For the substituent, a sulfamoyl group, an N-phenyl sulfamoyl group, an N,N-dimethyl sulfamoyl group, an N,N-diethyl sulfamoyl group, an N,N-dibutyl sulfamoyl group, an N,N-dihexyl sulfamoyl group, an N,N-diphenyl sulfamoyl group, an N-methyl-N-phenyl sulfamoyl group, an N-ethyl-N-phenyl sulfamoyl group, an N-methyl-N-tolyl sulfamoyl group, a morpholino sulfonyl group, a piperidino sulfonyl group and an N,N-bis(2-methoxyethyl) sulfonyl group are preferable, and a sulfamoyl group, an N-phenyl sulfamoyl group, an N,N-dibutyl sulfamoyl group, an N,N-diphenyl sulfamoyl group and an N-methyl-N-phenyl sulfamoyl group are more preferable.

In addition, the polymerizable compound of the present invention is preferably represented by the following formula (2).

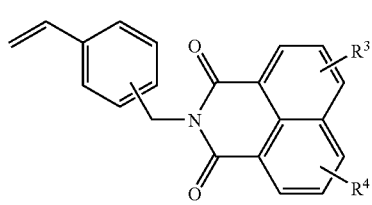

Formula (2)

In formula (2), $R^3$ and $R^4$ represent a monovalent substituent. $R^3$ and $R^4$ may be bound to each other to form a ring structure. Preferable examples of the substituent are the same as those described above in formula (1).

Preferable specific examples of the compound represented by formula (1) or formula (2) will be given below. The present invention is not limited to these examples.

<Exemplary Compounds>

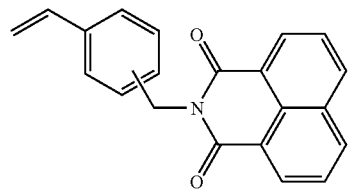

M-1

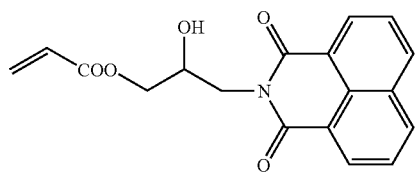

M-2

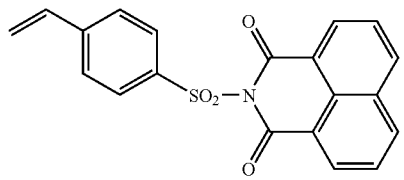

M-3

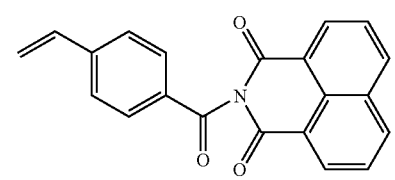

M-4

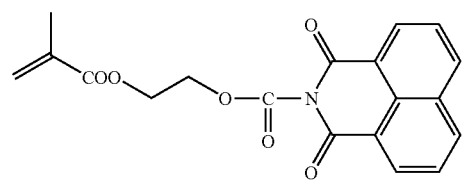

M-5

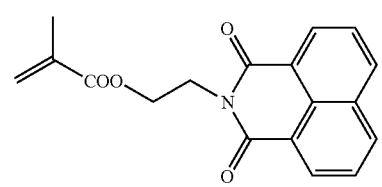

M-6

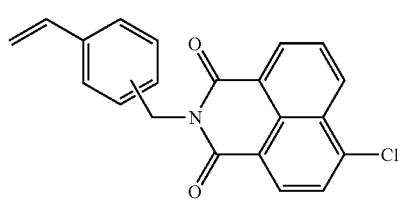

M-7

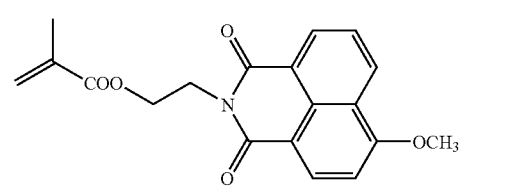

M-8

-continued

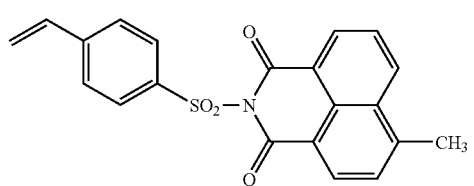

M-9

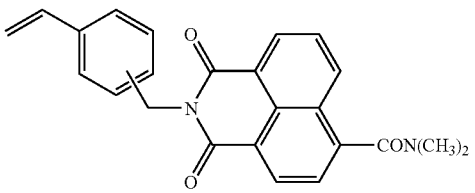

M-10

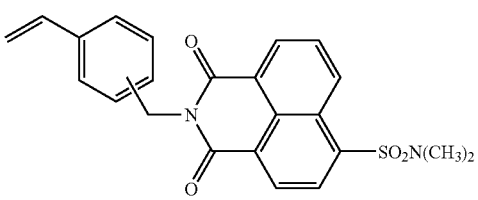

M-11

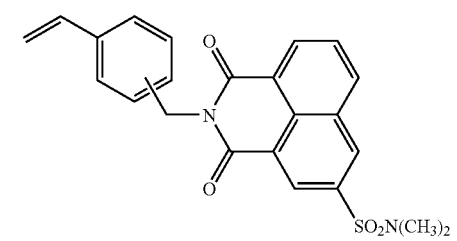

M-12

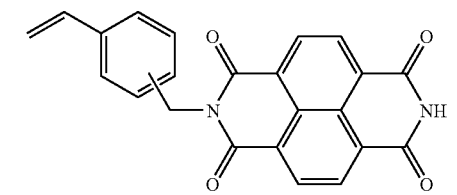

M-13

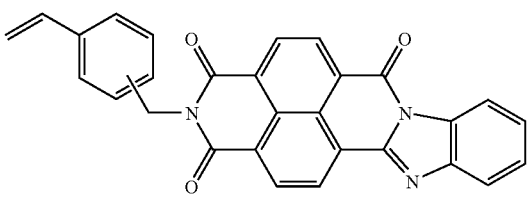

M-14

(Polymer)

The polymer of the present invention is a polymer that comprises a copolymer unit derived from the polymerizable compound (monomer) represented by the above formula (1) or formula (2).

The polymer is preferably a graft copolymer that contains, as a copolymer unit, a polymerizable oligomer having an ethylenically unsaturated double bond at its terminal.

Such a polymerizable oligomer having an ethylenically unsaturated double bond at its terminal is a compound having a given molecular mass and is therefore called a macromonomer.

The polymerizable oligomer contains a polymer chain moiety and a polymerizable functional group moiety at a terminal of the polymer chain. The polymerizable functional group moiety has an ethylenically unsaturated double bond. From the viewpoint of obtaining the desired graft copolymer, the group having an ethylenically unsaturated double bond is preferably present at only one of the terminals of the polymer chain. The group having an ethylenically unsaturated double bond is preferably a (meth)acryloyl group or a vinyl group, and more preferably a (meth)acryloyl group.

The polystyrene-equivalent number-average molecular mass (Mn) of the macromonomer is preferably in the range of 1,000 to 10,000, more preferably in the range of 2,000 to 9,000.

The polymer chain moiety is generally a homopolymer or copolymer formed from at least one monomer selected from the group consisting of alkyl (meth)acrylates, styrene and derivatives thereof, acrylonitrile, vinyl acetate, and butadiene, or is polyethylene oxide, polypropylene oxide, and polycaprolactone.

The polymerizable oligomer is preferably an oligomer represented by the following formula (3).

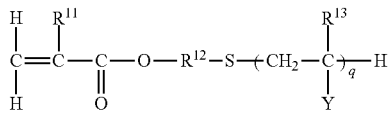

Formula (3)

In the formula (3), $R^{11}$ and $R^{13}$ each independently represent a hydrogen atom or a methyl group. $R^{12}$ represents an alkylene group having 1 to 12 carbon atoms (preferably an alkylene group having 2 to 4 carbon atoms, may have a substituent (for example, a hydroxyl group) and may be bound to each other via e.g. an ester bond, ether bond or amide bond). Y represents a phenyl group, a phenyl group with an alkyl group having 1 to 4 carbon atoms, or —COOR$^{14}$ (where $R^{14}$ represents an alkyl group having 1 to 6 carbon atoms, a phenyl group, or an arylalkyl group having 7 to 10 carbon atoms), and q is from 20 to 200. Y is preferably a phenyl group or —COOR$^{14}$ (where $R^{14}$ is an alkyl group having 1 to 12 carbon atoms.).

Preferable examples of the polymerizable oligomer (macromonomer) include polymers in which a (meth)acryloyl group is bound to one terminal of polymethyl (meth)acrylate, poly-n-butyl (meth)acrylate, poly-t-butyl (meth)acrylate or polystyrene. Examples of commercially available polymerizable oligomers include a polystyrene oligomer having a methacryloyl group at one terminal (Mn=6,000, trade name: AS-6, manufactured by Toagosei Co., Ltd.), a polymethyl methacrylate oligomer having a methacryloyl group at one terminal (Mn=6,000, trade name: AA-6, manufactured by Toagosei Co., Ltd.), and a poly-n-butylacrylate oligomer having a methacryloyl group at one terminal (Mn=6,000, trade name: AB-6, manufactured by Toagosei Co., Ltd.).

The polymerizable oligomer may be not only polymerizable oligomers represented by the formula (3) but also polymerizable oligomers represented by the following formula (4).

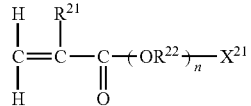

Formula (4)

In the above formula (4), $R^{21}$ represents a hydrogen atom or a methyl group, and $R^{22}$ represents an alkylene group having 1 to 8 carbon atoms. $X^{21}$ represents —$OR^{23}$ or —$COR^{24}$, where $R^{23}$ and $R^{24}$ represent a hydrogen atom, an alkyl group or an aryl group. n denotes a number from 2 to 200.

In the formula (4), $R^{21}$ represents a hydrogen atom or a methyl group. $R^{22}$ represents an alkylene group having 1 to 8 carbon atoms, is preferably an alkylene group having 1 to 6 carbon atoms and is more preferably an alkylene group having 2 to 3 carbon atoms. $X^{21}$ represents —$OR^{23}$ or —$OCOR^{24}$, where $R^{23}$ represents a hydrogen atom, an alkyl group having 1 to 18 carbon atoms, a phenyl group or a phenyl group substituted with an alkyl group having 1 to 18 carbon atoms. $R^{24}$ represents an alkyl group having 1 to 18 carbon atoms. Also, n denotes a number 2 to 200, preferably 5 to 100 and more preferably 10 to 100.

Examples of the polymerizable oligomer represented by the formula (4) include polyethylene glycol mono(meth)acrylate, polypropylene glycol mono(meth)acrylate, polyethylene glycol polypropylene glycol mono(meth)acrylate and polytetramethylene glycol monomethacrylate. These materials may be commercially available products or may be those synthesized properly.

The polymerizable monomers represented by the formula (4) are commercially available. Examples of these commercially available products include methoxypolyethylene glycol methacrylate (trade name: NK ESTER M-40G, M-90G and M-230G (manufactured by Toagosei Co., Ltd.); trade name: BLENMER-PME-100, PME-200, PME400, PME-1000, PME-2000 and PME4000 (manufactured by NOF CORPORATION)), polyethylene glycol monomethacrylate (trade name: BLENMER-PE-90, PE-200 and PE-350, manufactured by NOF CORPORATION), polypropylene glycol monomethacrylate (trade name: BLENMER-PP-500, PP-800 and PP-1000, manufactured by NOF CORPORATION), polyethylene glycol polypropylene glycol monomethacrylate (trade name: BLENMER-70PEP-370B, manufactured by NOF CORPORATION), polyethylene glycol polytetramethylene glycol monomethacrylate (trade name: BLENMER-55PET-800, manufactured by NOF CORPORATION) and polypropylene glycol polytetramethylene glycol monomethacrylate (trade name: BLENMER-NHK-5050, manufactured by NOF CORPORATION).

Further, the polymer for use in the present invention may be a copolymer with a monomer having a nitrogen atom. Examples of the monomer having a nitrogen atom include N,N-dimethylaminoethyl(meth)acrylate, N,N-dimethylaminopropyl(meth)acrylate, 1-(N,N-dimethylamino)-1,1-dimethylmethyl(meth)acrylate, N,N-dimethylaminohexyl(meth)acrylate, N,N-diethylaminoethyl(meth)acrylate, N,N-diisopropylaminoethyl(meth)acrylate, N,N-di-n-butylaminoethyl(meth)acrylate, N,N-di-i-butylaminoethyl(meth)acrylate, morpholinoethyl(meth)acrylate, piperidinoethyl(meth)acrylate, 1-pyrrolidinoethyl(meth)acrylate, N,N-methyl-2-pyrrolidylaminoethyl(meth)acrylate and N,N-methylphenylaminoethyl(meth)acrylate (the monomers mentioned above are (meth)acrylates); dimethyl(meth)acrylamide, diethyl(meth)acrylamide, diisopropyl (meth)acrylamide, di-n-butyl(meth)acrylamide, di-i-butyl(meth)acrylamide, morpholino(meth)acrylamide, piperidino(meth)acrylamide, N-methyl-2-pyrrolidyl(meth)acrylamide and N,N-methylphenyl(meth)acrylamide (the monomers mentioned above are (meth)acrylamides); 2-(N,N-dimethylamino)ethyl(meth)acrylamide, 2-(N,N-diethylamino)ethyl(meth)acrylamide, 3-(N,N-diethylamino)propyl(meth)acrylamide, 3-(N,N-dimethylamino)propyl(meth)acrylamide, 1-(N,N-dimethylamino)-1,1-dimethylmethyl(meth)acrylamide and 6(N,N-diethylamino)hexyl(meth)acrylamide (the monomers mentioned above are aminoalkyl(meth)acrylamides); p-vinylbenzyl-N,N-dimethylamine, p-vinylbenzyl-N,N-diethylamine, and p-vinylbenzyl-N,N-dihexylamine (the monomers mentioned above are vinylbenzylamines); and 2-vinylpyridine, 4-vinylpyridine, and N-vinylimidazole. Among these, N,N-dimethylaminoethyl(meth)acrylate, N,N-dimethylaminopropyl(meth)acrylate, 3-(N,N-diethylamino)propyl(meth)acrylamide, 3-(N,N-dimethylamino)propyl(meth)acrylamide, 2-vinylpyridine, 4-vinylpyridine, and N-vinylimidazole are preferable.

Further, the polymer for use in the present invention may be a copolymer with other monomers copolymerizable with these polymers. Examples of the other monomers copolymerizable with these polymers may include unsaturated carboxylic acids (for example, (meth)acrylic acids, crotonic acid, itaconic acid, maleic acid and fumaric acid), aromatic vinyl compounds (for example, styrene, α-methylstyrene, vinyltoluene, 2-vinylpyridine, 4-vinylpyridine and N-vinylimidazole), alkyl(meth)acrylates (for example, methyl(meth)acrylate, ethyl(meth)acrylate, n-butyl(meth)acrylate and i-butyl(meth)acrylate), alkylaryl(meth)acrylates (for example, benzyl(meth)acrylate), substituted alkyl(meth)acrylates (for example, glycidyl(meth)acrylate and 2-hydroxyethyl(meth)acrylate), vinyl carboxylates (for example, vinyl acetate and vinyl propionate), vinyl cyanates (for example, (meth)acrylonitrile and α-chloroacrylonitrile) and aliphatic conjugate dienes (for example, 1,3-butadiene and isoprene). Among these compounds, unsaturated carboxylic acids, alkyl(meth)acrylates, alkylaryl(meth)acrylates, vinyl carboxylates and aromatic vinyl compounds are preferable.

The polymer of the present invention is preferably a copolymer that comprises a copolymer unit derived from the polymerizable compound represented by the above formula (1) or (2) and a repeating unit given from the polymerizable oligomer (macromonomer), or a copolymer that comprises a repeating unit represented by the above formula (1), a repeating unit given from the polymerizable oligomer (macromonomer) and a repeating unit given from a monomer having a nitrogen atom. The above copolymer preferably contains the repeating unit represented by the formula (1) in a ratio 5% by weight to 70% by weight (particularly, 5% by weight to 30% by weight) based on all repeating units. In addition, the above copolymer preferably contains the repeating unit given from the polymerizable oligomer (macromonomer) in a ratio 30% by weight to 95% by weight (particularly, 50% by weight to 90% by weight) based on all repeating units. The above copolymer preferably contains the repeating unit derived from the above monomer containing nitrogen containing group in a ratio 5% by weight to 80% by weight (particularly, 5% by weight to 50% by weight) based on all repeating units.

When the additional monomer copolymerizable with these repeating units is used, the quantity of the repeating units derived from the additional monomer is preferably in the range of 5% by weight to 30% by weight based on the total quantity of the repeating units in the copolymer. The weight-average molecular mass (Mw) of the copolymer is preferably in the range of 1,000 to 200,000, more preferably in the range of 10,000 to 100,000. This weight-average molecular mass is a polystyrene equivalent weight-average molecular mass determined by gel permeation chromatography (carrier: tetrahydrofuran).

The structure of the copolymer can be analyzed, for example, by performing 1H-NMR measurement (a measurement using Mercury (300 MHz) manufactured by Varian, Inc.).

Examples of the graft copolymer that can be suitably used for the polymer of the present invention will be shown below; however, these examples are not intended to limit the present invention.

1) A copolymer of the monomer, represented by M-1 of the exemplary compounds, and polymethylmethacrylate having a methacryloyl group at its terminal
2) A copolymer of the monomer, represented by M-1 of the exemplary compounds, and polyethylene glycol mono(meth)acrylate
3) A copolymer of the monomer, represented by M-1 of the exemplary compounds, and polycaprolactone having a methacryloyl group at its terminal
4) A copolymer of the monomer, represented by M-1 of the exemplary compounds, and polybutyl acrylate having a methacryloyl group at its terminal
5) A copolymer of the monomer, represented by M-3 of the exemplary compounds, and polymethylmethacrylate having a methacryloyl group at its terminal
6) A copolymer of the monomer, represented by M-4 of the exemplary compounds, and polymethylmethacrylate having a methacryloyl group at its terminal
7) A copolymer of the monomer, represented by M-5 of the exemplary compounds, and polyethylene glycol mono(meth)acrylate
8) A copolymer of the monomer, represented by M-1 of the exemplary compounds, 3-(N,N-dimethylamino)propyl acrylamide, and polymethylmethacrylate having a methacryloyl group at its terminal
9) A copolymer of the monomer, represented by M-1 of the exemplary compounds, p-vinylbenzyl-N,N-dimethylamine, and polymethylmethacrylate having a methacryloyl group at its terminal
10) A copolymer of the monomer, represented by M-1 of the exemplary compounds, 3-(N,N-dimethylamino)propyl acrylamide, and polybutyl acrylate having a methacryloyl group at its terminal
11) A copolymer of the monomer, represented by M-1 of the exemplary compounds, 3-(N,N-dimethylamino)ethyl (meth)acrylate, and polymethylmethacrylate having a methacryloyl group at its terminal
12) A copolymer of the monomer, represented by M-1 of the exemplary compounds, 2-(N,N-dimethylamino)ethyl (meth)acrylate, and polymethylmethacrylate having a methacryloyl group at its terminal
13) A copolymer of the monomer, represented by M-1 of the exemplary compounds, 3-(N,N-dimethylamino)propyl acrylamide, polymethylmethacrylate having a methacryloyl group at its terminal, and polyethylene glycol mono(meth)acrylate
14) A copolymer of the monomer, represented by M-1 of the exemplary compounds, N,N-dimethylacrylamide, and polymethylmethacrylate having a methacryloyl group at its terminal
15) A copolymer of the monomer, represented by M-1 of the exemplary compounds, methyl (meth)acrylate, and polymethylmethacrylate having a methacryloyl group at its terminal
16) A copolymer of the monomer, represented by M-1 of the exemplary compounds, methacrylic acid, and polymethylmethacrylate having a methacryloyl group at its terminal
17) A copolymer of the monomer, represented by M-1 of the exemplary compounds, cyclohexyl (meth)acrylate, and polymethylmethacrylate having a methacryloyl group at its terminal
18) A copolymer of the monomer, represented by M-1 of the exemplary compounds, 2-hydroxyethyl (meth)acrylate, and polymethylmethacrylate having a methacryloyl group at its terminal
19) A copolymer of the monomer, represented by M-7 of the exemplary compounds, 3-(N,N-dimethylamino)propyl acrylamide, and polymethylmethacrylate having a methacryloyl group at its terminal
20) A copolymer of the monomer, represented by M-12 of the exemplary compounds, 3-(N,N-dimethylamino)propyl acrylamide, and polymethylmethacrylate having a methacryloyl group at its terminal
21) A copolymer of the monomer, represented by M-13 of the exemplary compounds, 3-(N,N-dimethylamino)ethyl (meth)acrylate, and polymethylmethacrylate having a methacryloyl group at its terminal Such graft copolymers can be obtained by radical polymerization, in a solvent, of the polymerizable oligomer and, optionally, the monomer having a nitrogen-containing group and/or other additional monomers. In this polymerization, a radical polymerization initiator is used in general. In addition to the initiator, a chain transfer agent (e.g., 2-mercaptoethanol and dodecyl mercaptan) may be further added for the synthesis of the graft copolymer.

(Ink Composition)

The ink composition of the present invention comprises, in addition to the polymer, at least (a) other polymerizable compound and (b) a pigment, and may comprise other components as necessary.

In the ink composition of the present invention, the polymers of the present invention may be used alone, or two or more may be used in combination. The content of the polymer in the ink composition is preferably 1% by mass to 100% by mass, more preferably 5% by mass to 50% by mass based on the amount of pigment to be added.

In the ink composition of the present invention, a known pigment dispersant may be used together in addition to the polymer of the present invention insofar as the effect of the present invention is not impaired. The amount of the known pigment dispersant to be added is preferably 50% by mass or less based on the polymer of the present invention.

It is preferable that the polymer of the present invention is used as a pigment dispersant. The structure having high affinity to a pigment due to a van-der-waals interaction ensures good adsorbing ability with respect to the pigment, making it possible to obtain a stable dispersant. Since the polymer is a high-molecular compound having a specified repeating structure, the steric repulsive effect of a high-molecular chain enables high dispersion stability.

Specific examples of the pigment include organic pigments such as a phthalocyanine base, insoluble azo base, azo lake base, anthraquinone base, quinacridone base, dioxazine base, diketopyrrolopyrrole base, anthrapyrimidine base, anthanthrone base, indanthrone base, flavanthrone base, perinone base, perylene base, thioindigo base and quinophthalone base.

The ink composition of the present invention is cured through the function of other polymerizable compound (a) when some energy is applied thereto. Preferably, the ink composition of the present invention contains (c) a polymerization initiator and is cured by irradiation with an active energy ray. The active energy ray is not particularly limited as long as it can impart energy which can generate initiating species in the ink composition by irradiation therewith. The energy ray include a wide range of energy rays such as α-rays, γ-rays, X-rays, ultraviolet rays, visible rays and electron rays. Among these energy rays, ultraviolet rays and electron rays are preferable, and ultraviolet rays are more preferable, from the viewpoint of curing sensitivity and the availability of equipment. Therefore, the ink composition of the present invention is preferably an ink composition which can be cured by irradiation with ultraviolet rays as the radiation ray.

<(a) Other Polymerizable Compound>

The curable ink composition of the present invention comprises other polymerizable compound (a). Any polymerizable compound may be used as the other polymerizable compound (a) without any particular limitation as long as it causes a polymerization reaction and is cured by supplying some energy. Though any of a monomer, oligomer and polymer may be used, in particular, various known polymerizable monomers known as a photo-cationic polymerizable monomer or photo-radical polymerizable monomer are preferable which causes a polymerization reaction by initiator species generated from the polymerization initiator (c) which is added as desired.

The polymerizable compounds may be used alone or two or more may be used in combination with the intention of adjusting, for example, reaction speed, ink properties and the properties of a cured film. Also, the polymerizable compounds may be either a monofunctional compound or a multifunctional compound.

Examples of cation-polymerizable monomers that can be used as the other polymerizable compound (a) include the epoxy compounds, vinyl ether compounds, and oxetane compounds described in JP-A Nos. 6-9714, 2001-31892, 2001-40068, 2001-55507, 2001-310938, 2001-310937 and 2001-220526.

Examples of monofunctional epoxy compounds that can be used as the cation-polymerizable monomer include phenyl glycidyl ether, p-tert-butylphenyl glycidyl ether, butyl glycidyl ether, 2-ethylhexyl glycidyl ether, allyl glycidyl ether, 1,2-butylene oxide, 1,3-butadiene monoxide, 1,2-epoxydodecane, epichlorohydrin, 1,2-epoxydecane, styrene oxide, cyclohexene oxide, 3-methacryloyloxymethylcyclohexene oxide, 3-acryloyloxymethylcyclohexene oxide, and 3-vinylcyclohexene oxide.

Examples of polyfunctional epoxy compounds that can be used as the cation-polymerizable monomer include bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexyl methyl-3',4'-epoxycyclohexane carboxylate, 2-(3,4-epoxycyclohexyl-5,5-spiro-3,4-epoxy)cyclohexane-metha-dioxane, bis(3,4-epoxycyclohexylmethyl)adipate, vinylcyclohexene oxide, 4-vinylepoxycyclohexane, bis(3,4-epoxy-6-methylcyclohexylmethyl) adipate, 3,4-epoxy-6-methylcyclohexyl-3',4'-epoxy-6'-methylcyclohexane carboxylate, methylenebis(3,4-epoxycyclohexane), dicylopentadiene diepoxide, ethyleneglycol di(3,4-epoxycyclohexylmethyl)ether, ethylenebis(3,4-epoxycyclohexane carboxylate), dioctyl epoxyhexahydrophthalate, di-2-ethylhexyl epoxyhexahydrophthalate, 1,4-butanediol diglycidyl ether, 1,6-hexanediol diglycidyl ether, glycerin triglycidyl ether, trimethylolpropane triglycidyl ether, polyethylene glycol diglycidyl ether, polypropylene glycol diglycidyl ethers, 1,1,3-tetradecadiene dioxide, limonene dioxide, 1,2,7,8-diepoxy octane, and 1,2,5,6-diepoxy cyclooctane.

Among these epoxy compounds, aromatic epoxides and alicyclic epoxides are preferable since they are advantageous in respect of the curing rate, alicyclic epoxides are more preferable.

Examples of monofunctional vinyl ether compounds that can be used as the cation-polymerizable monomer include methyl vinyl ether, ethyl vinyl ether, propyl vinyl ether, n-butyl vinyl ether, t-butyl vinyl ether, 2-ethylhexyl vinyl ether, n-nonyl vinyl ether, lauryl vinyl ether, cyclohexyl vinyl ether, cyclohexyl methyl vinyl ether, 4-methylcyclohexylmethyl vinyl ether, benzyl vinyl ether, dicyclopentenyl vinyl ether, 2-dicyclopentenoxy ethyl vinyl ether, methoxyethyl vinyl ether, ethoxyethyl vinyl ether, butoxyethyl vinyl ether, methoxyethoxyethyl vinyl ether, ethoxyethoxyethyl vinyl ether, methoxy polyethylene glycol vinyl ether, tetrahydrofurfuryl vinyl ether, 2-hydroxyethyl vinyl ether, 2-hydroxypropyl vinyl ether, 4-hydroxybutyl vinyl ether, 4-hydroxymethyl cyclohexylmethyl vinyl ether, diethylene glycol monovinyl ether, polyethylene glycol vinyl ether, chloroethyl vinyl ether, chlorobutyl vinyl ether, chloroethoxyethyl vinyl ether, phenylethyl vinyl ether, and phenoxy polyethylene glycol vinyl ether.

Examples of multifunctional vinyl ether compounds that can be used as the cation-polymerizable monomer include: divinyl ethers such as ethylene glycol divinyl ether, diethylene glycol divinyl ether, triethylene glycol divinyl ether, polyethylene glycol divinyl ether, propylene glycol divinyl ether, butylene glycol divinyl ether, hexane diol divinyl ether, bisphenol A alkylene oxide divinyl ether, and bisphenol F alkylene oxide divinyl ether; and multifunctional vinyl ethers such as trimethylolethane trivinyl ether, trimethylolpropane trivinyl ether, ditrimethylolpropane tetravinyl ether, glycerin trivinyl ether, pentaerythritol tetravinyl ether, dipentaerythritol pentavinyl ether, dipentaerythritol hexavinyl ether, ethylene oxide-added trimethylolpropane trivinyl ether, propylene oxide-added trimethylolpropane trivinyl ether, ethylene oxide-added ditrimethylolpropane tetravinyl ether, propylene oxide-added ditrimethylolpropane tetravinyl ether, ethylene oxide-added pentaerythritol tetravinyl ether, propylene oxide-added pentaerythritol tetravinyl ether, ethylene oxide-added dipentaerythritol hexavinyl ether, and propylene oxide-added dipentaerythritol hexavinyl ether.

Among the multifunctional vinyl ether compounds described above, a di- or trivinyl ether compound is preferable from the viewpoint of curing properties, adhesion to a recording medium, and the surface hardness of an image formed, and a divinyl ether compound is particularly preferable.

The oxetane compound that can be used as the cation-polymerizable monomer refers to a compound having an oxetane ring. Such an oxetane compound may be selected arbitrarily from known oxetane compounds, for example, those described in JP-A Nos. 2001-220526, 2001-310937, and 2003-341217. The compound having an oxetane ring is preferably a compound having 1 to 4 oxetane rings in its structure. By using such a compound, the viscosity of the ink composition can be maintained in a range which enables easy handling, and the ink after curing adheres strongly to the recording medium.

Examples of monofunctional oxetanes that can be used as the cation-polymerizable monomer include 3-ethyl-3-hydroxymethyl oxetane, 3-(meth)allyloxymethyl-3-ethyl oxetane, (3-ethyl-3-oxetanylmethoxy)methyl benzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl)ether, 2-ethylhexyl(3-ethyl-3-oxetanylmethyl)ether, ethyldiethylene glycol(3-ethyl-3-oxetanylmethyl)ether, dicyclopentadiene (3-ethyl-3-oxetanylmethyl)ether, dicyclopentenyloxyethyl (3-ethyl-3-oxetanylmethyl)ether, dicyclopentenyl (3-ethyl-3-oxetanylmethyl)ether, tetrahydrofurfuryl (3-ethyl-3-oxetanylmethyl)ether, tetrabromophenyl (3-ethyl-3-oxetanylmethyl)ether, 2-tetrabromophenoxyethyl (3-ethyl-3-oxetanylmethyl)ether, tribromophenyl (3-ethyl-3-oxetanylmethyl)ether, 2-tribromophenoxyethyl (3-ethyl-3-oxetanylmethyl)ether, 2-hydroxyethyl (3-ethyl-3-oxetanylmethyl)ether, 2-hydroxypropyl (3-ethyl-3-oxetanylmethyl)ether, butoxyethyl (3-ethyl-3-oxetanylmethyl)ether, pentachlorophenyl (3-ethyl-3-oxetanylmethyl)ether, pentabromophenyl (3-ethyl-3-oxetanylmethyl)ether, and bornyl(3-ethyl-3-oxetanylmethyl) ether.

Examples of multifunctional oxetanes that can be used as the cation-polymerizable monomer include 3,7-bis(3-oxetanyl)-5-oxa-nonane, 3,3'-(1,3-(2-methylenyl) propanediylbis (oxymethylene)) bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl)ether, dicyclopentenyl bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene (3-ethyl-3-oxetanylmethyl)ether, trimethylolpropane tris(3-ethyl-3-oxetanylmethyl)ether, 1,4-bis(3-ethyl-3-oxetanylmethoxy) butane, 1,6-bis(3-ethyl-3-oxetanylmethoxy) hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis(3-ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, EO-modified bisphenol A bis(3-ethyl-3-oxetanylmethyl) ether, PO-modified bisphenol A bis(3-ethyl-3-oxetanylmethyl)ether, EO-modified hydrogenated bisphenol A bis(3-ethyl-3-oxetanylmethyl)ether, PO-modified hydrogenated bisphenol A bis(3-ethyl-3-oxetanylmethyl)ether, and EO-modified bisphenol F (3-ethyl-3-oxetanylmethyl)ether.

Such compounds having an oxetane ring are described in detail in columns [0021] to [0084] of JP-A 2003-341217 mentioned above, and the compounds described therein can be suitably used in the present invention as well.

Among the oxetane compounds as the cation-polymerizable monomer, a compound having one or two oxetane rings is preferable from the viewpoint of the viscosity and adhesiveness of the ink composition.

In the ink composition of the present invention, as a cation-polymerizable monomer, only one compound may be used, or two or more compounds may be used in combination. From the viewpoint of effective suppression of shrinkage upon curing, it is preferable to use a combination of at least one oxetane compound and at least one compound selected from epoxy compounds and vinyl ether compounds.

In the present invention, the other polymerizable compound (a) may be selected from a wide variety of known radical polymerizable monomers that undergo polymerization reaction in the presence of an initiator species generated from a photoradical initiator.

Examples of such radical polymerizable monomers include (meth)acrylates, (meth)acrylamides, and aromatic vinyls. In the specification, the term "(meth)acrylate" is occasionally used to mean "acrylate" and/or "methacrylate", and the term "(meth)acryl" is occasionally used to mean "acryl" and/or "methacryl".

Examples of (meth)acrylates that can be used as the radical polymerizable monomer include monofunctional (meth) acrylates, bifunctional (meth)acrylates, trifunctional (meth) acrylates, tetrafunctional (meth)acrylates, pentafunctional (meth)acrylates, and hexafunctional (meth)acrylates.

Examples of monofunctional (meth)acrylates include hexyl (meth)acrylate, 2-ethylhexyl (meth)acrylate, tert-octyl (meth)acrylate, isoamyl (meth)acrylate, decyl (meth)acrylate, isodecyl (meth)acrylate, stearyl (meth)acrylate, isostearyl (meth)acrylate, cyclohexyl (meth)acrylate, 4-n-butylcyclohexyl (meth)acrylate, bornyl (meth)acrylate, isobornyl (meth)acrylate, benzyl (meth)acrylate, 2-ethylhexyldiglycol (meth)acrylate, butoxyethyl (meth)acrylate, 2-chloroethyl (meth)acrylate, 4-bromobutyl (meth)acrylate, cyanoethyl (meth)acrylate, benzyl (meth)acrylate, butoxymethyl (meth) acrylate, 3-methoxybutyl (meth)acrylate, alkoxymethyl (meth)acrylate, alkoxyethyl (meth)acrylate, 2-(2-methoxyethoxy)ethyl (meth)acrylate, 2-(2-butoxyethoxy)ethyl (meth)acrylate, 2,2,2-tetrafluoroethyl (meth)acrylate, 1H,1H,2H,2H-perfluorodecyl (meth)acrylate, 4-butylphenyl (meth)acrylate, phenyl (meth)acrylate, 2,4,5-tetramethylphenyl (meth)acrylate, 4-chlorophenyl (meth)acrylate, phenoxymethyl (meth)acrylate, phenoxyethyl (meth)acrylate, glycidyl (meth)acrylate, glycidyloxybutyl (meth)acrylate, glycidyloxyethyl (meth)acrylate, glycidyloxypropyl (meth) acrylate, tetrahydrofurfuryl (meth)acrylate, hydroxyalkyl (meth)acrylate, 2-hydroxyethyl (meth)acrylate, 3-hydroxypropyl (meth)acrylate, 2-hydroxypropyl (meth)acrylate, 2-hydroxybutyl (meth)acrylate, 4-hydroxybutyl (meth)acrylate, 3-hydroxybutyl (meth)acrylate, dimethylaminoethyl (meth)acrylate, diethylaminoethyl (meth)acrylate, dimethylaminopropyl (meth)acrylate, diethylaminopropyl (meth) acrylate, trimethoxysilylpropyl (meth)acrylate, trimethylsilylpropyl (meth)acrylate, polyethylene oxide monomethyl ether (meth)acrylate, oligoethylene oxide monomethyl ether (meth)acrylate, polyethylene oxide (meth)acrylate, oligoethylene oxide (meth)acrylate, oligoethylene oxide monoalkyl ether (meth)acrylate, polyethylene oxide monoalkyl ether (meth)acrylate, dipropylene glycol (meth)acrylate, polypropylene oxide monoalkyl ether (meth)acrylate, oligopropylene oxide monoalkyl ether (meth)acrylate, 2-methacryloyloxytylsuccinic acid, 2-methacryloyloxyhexahydrophthalic acid, 2-methacryloyloxyethyl-2-hydroxypropyl phthalate, butoxydiethylene glycol (meth)acrylate, trifluoroethyl (meth)acrylate, perfluorooctylethyl (meth)acrylate, 2-hydroxy-3-phenoxypropyl (meth)acrylate, EO-modified phenol (meth)acrylate, EO-modified cresol (meth)acrylate, EO-modified nonyl phenol (meth)acrylate, PO-modified nonyl phenol (meth)acrylate, EO-modified 2-ethylhexyl (meth) acrylate, dicyclopentenyl (meth)acrylate, and dicyclopentanyl (meth)acrylate.

Examples of bifunctional (meth)acrylates include 1,6-hexanediol di(meth)acrylate, 1,10-decanediol di(meth)acrylate, neopentyl glycol di(meth)acrylate, 2,4-dimethyl-1,5-pentanediol di(meth)acrylate, butylethylpropanediol (meth) acrylate, ethoxylated cyclohexane methanol di(meth)acrylate, polyethylene glycol di(meth)acrylate, oligoethylene glycol di(meth)acrylate, ethylene glycol di(meth)acrylate, 2-ethyl-2-butyl-butanediol di(meth)acrylate, hydroxypivalic acid neopentyl glycol di(meth)acrylate, EO-modified bisphenol A di(meth)acrylate, bisphenol F polyethoxy di(meth)acrylate, polypropylene glycol di(meth)acrylate, oligopropylene glycol di(meth)acrylate, 1,4-butanediol di(meth)acrylate, 2-ethyl-2-butylpropanediol di(meth)acrylate, 1,9-nonane di(meth)acrylate, propoxylated ethoxylated bisphenol A di(meth)acrylate, tricyclodecane di(meth)acrylate, neopentyl glycol propyleneoxy diacrylate, dipropylene glycol di(meth)acrylate, and propoxylated neopentyl glycol di(meth)acrylate.

Examples of trifunctional (meth)acrylates include trimethylolpropane tri(meth)acrylate, trimethylolethane tri(meth)acrylate, trimethylolpropane alkylene oxide-modified tri(meth)acrylate, pentaerythritol tri(meth)acrylate, dipentaerythritol tri(meth)acrylate, trimethylolpropane tri((meth)acryloyloxypropyl)ether, isocyanuric acid alkylene oxide-modified tri(meth)acrylate, propionic acid dipentaerythritol tri(meth)acrylate, tri((meth)acryloyloxyethyl) isocyanurate, hydroxypival aldehyde-modified dimethylolpropane tri(meth)acrylate, sorbitol tri(meth)acrylate, propoxylated trimethylolpropane tri(meth)acrylate, and ethoxylated glycerin triacrylate.

Examples of tetrafunctional (meth)acrylates include pentaerythritol tetra(meth)acrylate, sorbitol tetra(meth)acrylate, ditrimethylolpropane tetra(meth)acrylate, propionic acid dipentaerythritol tetra(meth)acrylate, and ethoxylated pentaerythritol tetra(meth)acrylate.

Examples of pentafunctional (meth)acrylates include sorbitol penta(meth)acrylate and dipentaerythritol penta(meth)acrylate.

Examples of hexafunctional (meth)acrylates include dipentaerythritol hexa(meth)acrylate, sorbitol hexa(meth)acrylate, phosphazene alkylene oxide-modified hexa(meth)acrylate, and caprolactone-modified dipentaerythritol hexa(meth)acrylate.

Examples of (meth)acrylamides that can be used as the radical polymerizable monomer include (meth)acrylamide, N-methyl (meth)acrylamide, N-ethyl (meth)acrylamide, N-propyl (meth)acrylamide, N-n-butyl (meth)acrylamide, N-t-butyl (meth)acrylamide, N-butoxymethyl (meth)acrylamide, N-isopropyl (meth)acrylamide, N-methylol (meth)acrylamide, N,N-dimethyl (meth)acrylamide, N,N-diethyl (meth)acrylamide, and (meth)acryloyl morpholine.

Examples of aromatic vinyls that can be used as the radical polymerizable monomer include styrene, methyl styrene, dimethyl styrene, trimethyl styrene, ethyl styrene, isopropyl styrene, chloromethyl styrene, methoxy styrene, acetoxy styrene, chlorostyrene, dichlorostyrene, bromostyrene, methyl vinylbenzoate, 3-methyl styrene, 4-methyl styrene, 3-ethyl styrene, 4-ethyl styrene, 3-propyl styrene, 4-propyl styrene, 3-butyl styrene, 4-butyl styrene, 3-hexyl styrene, 4-hexyl styrene, 3-octyl styrene, 4-octyl styrene, 3-(2-ethylhexyl) styrene, 4-(2-ethylhexyl) styrene, allyl styrene, isopropenyl styrene, butenyl styrene, octenyl styrene, 4-t-butoxycarbonyl styrene, 4-methoxy styrene, and 4-t-butoxy styrene.

Examples of the radical polymerizable monomer in the present invention include vinyl esters [vinyl acetate, vinyl propionate, vinyl versate etc.], allyl esters [allyl acetate etc.], halogen-containing monomers [vinylidene chloride, vinyl chloride etc.], vinyl ethers [methyl vinyl ether, butyl vinyl ether, hexyl vinyl ether, methoxy vinyl ether, 2-ethyl hexyl vinyl ether, methoxyethyl vinyl ether, cyclohexyl vinyl ether, chloroethyl vinyl ether, triethyleneglycol divinyl ether etc.] and vinyl cyanides [(meth)acrylonitrile etc.], and olefins [ethylene, propylene etc.].

Among these, the radical polymerizable monomer in the present invention is preferably (meth)acrylates or (meth)acrylamides from the viewpoint of the curing rate, and more preferably a tetrafunctional or higher-functional (meth)acrylate from the viewpoint of the curing rate. From the viewpoint of the viscosity of the ink composition, it is preferable to use a combination of a multifunctional (meth)acrylate such as described above and a monofunctional or bifunctional (meth)acrylate or (meth)acrylamide.

Appropriate amount of the other polymerizable compound (a) in the ink composition is 50% by mass to 95% by mass, based on the total solid content of the composition; preferably, the content of the other polymerizable compound (a) in the ink composition is 60% by mass to 92% by mass, still preferably 70% by mass to 90% by mass, based on the total solid content of the composition <(b) Pigment>

The ink composition of the present invention contains a pigment as an essential component. Owing to the function of the polymer, fine pigment particles with a small particle diameter are dispersed uniformly and stably in the ink composition, which allows the formation of sharp images excellent in coloring property.

The pigment is not particularly limited and may be appropriately selected from a wide variety of known pigments and dyes according to the purpose. Because the pigment is contained as a colorant, the images obtained by using the ink composition of the present invention are excellent in weather resistance.

The pigment contained in the ink composition of the present invention is not particularly limited. Organic pigments and inorganic pigments that are usually available on the market and also, pigments obtained by dyeing resin particles with dyes may be used. In addition, commercially available pigment dispersants and surface treated pigments, for example, those obtained by dispersing pigments in an insoluble resin as a dispersion medium or those obtained by grafting a resin on the surface of a pigment may be used insofar as they do not impair the effect of the present invention.

Examples of these pigments include the pigments described, for example, in Seijiro Itoh, "Dictionary of Pigments" (2000), W. Herbst and K. Hunger, "Industrial Organic Pigments", and JP-A Nos. 2002-12607, 2002-188025, 2003-26978, and 2003-342503.

Examples of the organic and inorganic pigments contained in the ink composition of the present invention include the following. Examples of pigments of yellow color include: monoazo pigments such as C.I. Pigment Yellow 1 (Fast Yellow G, etc.) and C.I. Pigment Yellow 74; disazo pigments such as C.I. Pigment Yellow 12 (Disazo Yellow, etc.), C.I. Pigment Yellow 17, C.I. Pigment Yellow 97, C.I. Pigment Yellow 3, C.I. Pigment Yellow 16, C.I. Pigment Yellow 83, C.I. Pigment Yellow 155, and C.I. Pigment Yellow 219; non-benzidine azo pigments such as C.I. Pigment Yellow 180; azolake pigments such as C.I. Pigment Yellow 100 (tartrazine yellow lake, etc.); condensation azo pigments such as C.I. Pigment Yellow 95 (Condensation Azo Yellow, etc.), C.I. Pigment Yellow 93, C.I. Pigment Yellow 94, C.I. Pigment Yellow 128, and C.I. Pigment Yellow 166; acidic-dye lake pigments such as C.I. Pigment Yellow 115 (quinoline yellow lake, etc.); basic-dye lake pigments such as C.I. Pigment Yellow 18 (thioflavin lake, etc.); anthraquinone pigments such as C.I. Pigment Yellow 24 (fravantrone yellow, etc.); quinophtharone pigments such as C.I. Pigment Yellow 110 (quinophtharone yellow, etc.); isoindoline pigments such as C.I. Pigment Yellow 139 (isoindoline yellow, etc.); pyrazolone pigments such as C.I. Pigment Yellow 60 (pyrazolone yellow, etc.); acetolone pigments such as C.I. Pigment Yellow 120, C.I. Pigment Yellow 154, C.I. Pigment Yellow 167, C.I. Pigment Yellow 151, C.I. Pigment Yellow 175, C.I. Pigment Yellow 180, C.I. Pigment Yellow 181, and C.I. Pigment Yellow 194; metal-complex-salt pigments such as C.I. Pigment Yellow 150; nitroso pigments such as C.I. Pigment Yellow 153 (nickel nitroso yellow, etc.); and metal-complex-salt azomethine pigments such as C.I. Pigment Yellow 117 (copper azomethine yellow, etc.).

Examples of pigments of red or magenta color include: monoazo pigments such as C.I. Pigment Red 3 (toluidine red, etc.); B-naphthol pigments such as C.I. Pigment Red 1, C.I. Pigment Red 4, and C.I. Pigment Red 6; disazo pigments such as C.I. Pigment Red 38 (Pyrazolone Red B, etc.); azolake pigments such as C.I. Pigment Red 53:1 (Lake Red C, etc.), C.I. Pigment Red 57:1 (Brilliant Carmine 6B, etc.), C.I. Pigment Red 52:1, and C.I. Pigment Red 48 (B-oxynaphthoic acid Lake, etc.); condensation azo pigments such as C.I. Pigment Red 144, C.I. Pigment Red 166, C.I. Pigment Red 220, C.I. Pigment Red 214, C.I. Pigment Red 221, and C.I. Pigment Red 242 (Condensation Azo Red, etc.); acidic dye lake pigments such as C.I. Pigment Red 174 (Phloxine B Lake, etc.) and C.I. Pigment Red 172 (Erythrosine Lake, etc.); basic dye lake pigments such as C.I. Pigment Red 81 (Rhodamine 6G' Lake, etc.); anthraquinone pigments such as C.I. Pigment Red 177 (dianthraquinolyl red, etc.); thioindigo pigments such as C.I. Pigment Red 88 (Thioindigo Bordeaux, etc.); perynone pigments such as C.I. Pigment Red 194 (perynone red, etc.); perylene pigments such as C.I. Pigment Red 149, C.I. Pigment Red 179, C.I. Pigment Red 178, C.I. Pigment Red 190, C.I. Pigment Red 224, and C.I. Pigment Red 123; quinacridone pigments such as C.I. Pigment Violet 19 (unsubstituted quinacridone), C.I. Pigment Red 122, C.I. Pigment Red 262, C.I. Pigment Red 207, and C.I. Pigment Red 209; isoindolinone pigments such as C.I. Pigment Red 180 (Isoindolinone Red 2BLT, etc.); alizarin lake pigments such as C.I. Pigment Red 83 (madder lake, etc.); naphtholone pigments such as C.I. Pigment Red 171, C.I. Pigment Red 175, C.I. Pigment Red 176, C.I. Pigment Red 185, and C.I. Pigment Red 208; naphthol AS lake pigments such as C.I. Pigment Red 247; naphthol AS pigments such as C.I. Pigment Red 2, C.I. Pigment Red 5, C.I. Pigment Red 21, C.I. Pigment Red 170, C.I. Pigment Red 187, C.I. Pigment Red 256, C.I. Pigment Red 268, and C.I. Pigment Red 269; and diketopyrrolopyrrole pigments such as C.I. Pigment Red 254, C.I. Pigment Red 255, C.I. Pigment Red 264, and C.I. Pigment Red 272.

Examples of blue or cyan pigments include disazo pigments such as C.I. Pigment Blue 25 (dianisidine blue, etc.); phthalocyanine pigments such as C.I. pigment blue 15, C.I. pigment blue 15:1, C.I. pigment blue 15:2, C.I. pigment blue 15:3, C.I. pigment blue 15:4, C.I. pigment blue 15:6, and C.I. pigment blue 16 (phthalocyanine blue, etc.); acidic dye lake pigments such as C.I. pigment blue 24 (peacock blue lake, etc.); basic dye lake pigments such as C.I. Pigment Blue 1 (Victoria Pure Blue BO Lake, etc.); anthraquinone pigments such as C.I. pigment blue 60 (indanthron blue, etc.); and alkali blue pigments such as C.I. Pigment Blue 18 (alkali blue V-5:1).

Examples of green pigments include phthalocyanine pigments such as C.I. Pigment Green 7 (phthalocyanine green) and C.I. Pigment Green 36 (phthalocyanine green); and azo metal complex pigments such as C.I. Pigment Green 8 and C.I. Pigment Green 10.

Examples of orange pigments include isoindoline pigments such as C.I. Pigment Orange 66 (isoindoline orange); anthraquinone pigments such as C.I. Pigment Orange 51 (dichloropyranthron orange); B-naphthol pigments such as C.I. Pigment Orange 2, C.I. Pigment Orange 3, and C.I. Pigment Orange 5; naphthol AS pigments such as C.I. Pigment Orange 4, C.I. Pigment Orange 22, C.I. Pigment Orange 24, C.I. Pigment Orange 38, and C.I. Pigment Orange 74; isoindolinone pigments such as C.I. Pigment Orange 61; perynone pigments such as C.I. Pigment Orange 43; disazo pigments such as C.I. Pigment Orange 15 and C.I. Pigment Orange 16; quinacridone pigments such as C.I. Pigment Orange 48 and C.I. Pigment Orange 49; acetolone pigments such as C.I. Pigment Orange 36, C.I. Pigment Orange 62, C.I. Pigment Orange 60, C.I. Pigment Orange 64, and C.I. Pigment Orange 72; and pyrazolone pigments such as C.I. Pigment Orange 13 and C.I. Pigment Orange 34.

Examples of brown pigments include naphtholone pigments such as C.I. Pigment Brown 25 and C.I. Pigment Brown 32.

Examples of violet pigments include naphtholone pigments such as C.I. Pigment Violet 32; perylene pigments such as C.I. Pigment Violet 29; naphthol AS pigments such as C.I. Pigment Violet 13, C.I. Pigment Violet 17, and C.I. Pigment Violet 50; and dioxazine pigments such as C.I. Pigment Violet 23 and C.I. Pigment Violet 37.

Examples of black pigments include indazine pigments such as carbon black, titanium black, and C.I. Pigment Black 1 (aniline black); and perylene pigments such as C.I. Pigment Black 31 and C.I. Pigment Black 32.

Examples of white pigments include basic lead carbonate ($2PbCO_3Pb(OH)_2$, so-called silver white), zinc oxide (ZnO, so-called zinc white), titanium oxide ($TiO_2$, so-called titanium white), and strontium titanate ($SrTiO_3$, so-called titanium strontium white). The inorganic particles to be used for white pigment may be particles of a simple substance, or may be an oxide of, for example, silicon, aluminum, zirconium, or titanium, or composite particles with an organometallic compound or an organic compound.

Since titanium oxide has a lower specific gravity and a higher refractive index than other white pigments and is more stable chemically or physically, titanium oxide has a greater masking and coloring potential as a pigment, and is further excellent in resistance to acid or alkali and other environmental factors. Thus, the use of titanium oxide as a white pigment is preferable. Of course, other white pigment (including white pigments other than those described above) may be used as necessary.

For dispersing the pigment, dispersing machines such as a ball mill, a sand mill, an attriter, a roll mill, a jet mill, a homogenizer, a paint shaker, a kneader, an agitator, a Henschel mixer, a colloid mill, an ultrasonic wave homogenizer, a pearl mill, and a wet jet mill, can be used.

When the pigment is dispersed, it is preferable to add the polymer of the present invention.

A synergist suitable for the pigment may be used as a dispersing aid as necessary. The dispersing aid is preferably added in an amount of 1 part by mass to 50 parts by mass based on 100 parts by mass of the pigment.

In the ink composition, a solvent may be added as the dispersion medium for various components such as pigment, or the other polymerizable compound (a), which is a low-molecular-mass component, may be used as a solvent-free dispersion medium. The ink composition according to the present invention is preferably free of solvent because the composition is preferably a radiation-curable ink that is cured after applied onto a recording medium. If the solvent remains in the cured ink image, solvent resistance may be deteriorated and a problem of VOC (Volatile Organic Compound) may occur. Thus, the dispersion medium is preferably a other polymerizable compound (a), particularly preferably a polymerizable compound having the lowest viscosity, in view of the improvement in the dispersibility and handling property of the ink composition.

A pigment having a smaller diameter is more excellent in coloring properties. Therefore, the average particle diameter of the pigment to be used is preferably in the range of about 0.01 µm to 0.4 µm, more preferably in the range of 0.02 µm to 0.2 µm. The maximum particle diameter may be 3 µm, preferably 1 µm; such a maximum particle diameter can be achieved by appropriate selections of the pigment (b), the dispersant, the dispersing medium, the dispersion conditions, and the filtration conditions. By controlling the particle diameter, clogging in a head nozzle can be prevented, and the storage stability of ink, the transparency of ink, and the curing sensitivity can be secured. Because the polymer excellent in dispersibility and stability is used in the present invention, a uniform and stable dispersion can be obtained even when fine pigment particles are used.

The particle diameter of the pigment in the ink composition can be measured by a known measurement method. Specifically, the particle diameter can be measured by a centrifugal-sedimentation light-transmission method, an X-ray transmission method, a laser diffraction/scattering method, or a dynamic light scattering method.

When the pigment is an organic pigment, the amount of the pigment in the ink composition is preferably 1% by mass to 20% by mass, more preferably 2% by mass to 10% by mass, in terms of solid content. When the pigment is an inorganic pigment, the amount of the pigment in the ink composition is preferably 1% by mass to 30% by mass, more preferably 2% by mass to 25% by mass, in terms of solid content.

In the ink composition of the present invention, various additives may be used additionally according to the purpose, in addition to the above-described essential components. These optional components are described.

<(c) Polymerization Initiator>

The ink composition of the present invention preferably contains a radical polymerization initiator or a cation polymerization initiator and more preferably contains a photopolymerization initiator.

The photopolymerization initiator in the present invention is a compound that is changed chemically through the action of light or an interaction with a sensitizing dye put in an electron excited state to produce at least one of a radical, an acid and a base.

The photopolymerization initiator may be selected appropriately from initiators having sensitivity to the activated ray for irradiation, such as UV ray at 400 nm to 200 nm, far UV ray, g-line, h-line, i-line, KrF excimer laser light, ArF excimer laser light, electron ray, X-ray, molecular beam, or ion beam.

For the photopolymerization initiator, any of common photopolymerization initiators known in the art may be used. Examples thereof are described, for example, in Bruce M. Monroe et al., Chemical Revue, 93, 435 (1993); R. S. Davidson, Journal of Photochemistry and biology A: Chemistry, 73, 81 (1993); J. P. Faussier, "Photoinitiated Polymerization-Theory and Applications": Rapra Review vol. 9, Report, Rapra Technology (1998); and M. Tsunooka et al., Prog. Polym. Sci., 21, 1 (1996). Compounds favorably used in chemical amplification photoresists and for photocationic polymerization are described in Japanese Research Association for Organic Electronics Materials Ed., "Organic Materials for Imaging" (published by Bun-Shin Shuppan (1993), pp. 187 to 192), and those compounds can be used. The compounds that undergo oxidative or reductive bond cleavage through the interaction with the electronically-excited state of sensitizing dye are also known, and described, for example in F. D. Saeva, Topics in Current Chemistry, 156, 59 (1990); G. G. Maslak, Topics in Current Chemistry, 168, 1 (1993); H. B. Shuster et al., JACS, 112, 6329 (1990); and I. D. F. Eaton et al., JACS, 102, 3298 (1980).

Examples of such photopolymerization initiators include (i) aromatic ketones, (ii) aromatic onium salt compounds, (iii) organic peroxides, (iv) hexaarylbiimidazole compounds, (v) ketoxime ester compounds, (vi) borate compounds, (vii) azinium compounds, (viii) metallocene compounds, (ix) active ester compounds, and (x) compounds containing a carbon-halogen bond.

In addition, acylphosphine oxide may also be used as the photopolymerization initiator.

For the aromatic ketones (i), the compounds each having a benzophenone or thioxanthone skeleton described, for example in "Radiation Curing in Polymer Science and Technology" J. P. Fouassier and J. F. Rabek (1993), pp. 77 to 117 are preferable; and α-thio benzophenone compounds described in Japanese Patent Application Publication (JP-B) No. 47-6416; the benzoin ether compounds described in JP-B No. 47-3981; the α-substituted benzoin compounds described in JP-B No. 47-22326; the benzoin derivatives described in JP-B No. 47-23664; the aroyl phosphonic acid esters described in JP-A No. 57-30704; the dialkoxybenzophenones described in JP-B No. 60-26483; the benzoin ethers described in JP-B No. 60-26403 and JP-A No. 62-81345; the α-amino benzophenones described in JP-B No. 1-34242, U.S. Pat. No. 4,318,791, and EP Patent No. 0284561A1; p-di(dimethylaminobenzoyl)benzene described in JP-A No. 2-211452; the thio-substituted aromatic ketones described in JP-A No. 61-194062; the acylphosphine sulfides described in JP-B No. 2-9597; the acylphosphines described in JP-B No. 2-9596; the thioxanthones described in JP-B No. 63-61950; the coumarins described in JP-B No. 5942864; monoacylphosphineoxide described in JP-B Nos. 60-8047 and 6340799; and bisacylphosphineoxide described in JP-A Nos. 3-101686, 5-345790 and 6-298818 are more preferable.

Examples of the aromatic onium salt compounds (II) include aromatic onium salts of the elements in Groups V, VI and VII in the periodic table, specifically, aromatic onium salts of N, P, As, Sb, Bi, O, S, Se, Te, and I. For example, the iodonium salts described in EP Patent No. 104143, U.S. Pat. No. 4,837,124, and JP-A Nos. 2-150848 and 2-96514; the sulfonium salts described in EP Patent Nos. 370693, 233567, 297443, 297442, 279210, and 422570 and U.S. Pat. Nos. 3,902,144, 4,933,377, 4,760,013, 4,734,444, and 2833827; diazonium salts (e.g., benzene diazonium salts which may have one or more substituted groups); diazonium salt resins (e.g., formaldehyde resins of diazodiphenylamine); N-alkoxypyridinium salts (e.g., those described in U.S. Pat. No. 4,743,528, JP-A Nos. 63-138345, 63-142345, and 63-142346, and JP-B No. 4642363, and specifically, 1-methoxy-4-phenylpyridinium tetrafluoroborate, etc.); and the compounds described in JP-B Nos. 52-147277, 52-14278, and 52-14279 are suitably used. The aromatic onium salt compound (II) generates a radical or an acid as an active species.

Examples of the organic peroxides (iii) include almost all organic compounds having one or more oxygen-oxygen bonds in the molecule; and preferable examples thereof include peroxide esters such as 3,3',4,4'-tetra-(t-butylperoxycarbonyl)benzophenone, 3,3',4,4'-tetra-(t-amylperoxycarbonyl)benzophenone, 3,3',4,4'-tetra-(t-hexylperoxycarbonyl) benzophenone, 3,3',4,4'-tetra-(t-octylperoxycarbonyl) benzophenone, 3,3',4,4'-tetra-(cumylperoxycarbonyl)

benzophenone, 3,3',4,4'-tetra-(p-isopropyl cumylperoxycarbonyl)benzophenone, and di-t-butyl diperoxyisophthalate.

Examples of the hexaarylbiimidazole compounds (iv) include the Rofin dimers described in JP-B Nos. 45-37377 and 44-86516, such as 2,2'-bis(o-chlorophenyl)-4,4',5,5'-tetraphenylbiimidazole, 2,2'-bis(o-bromophenyl)-4,4',5,5'-tetraphenylbiimidazole, 2,2'-bis(o-,p-dichlorophenyl)-4,4',5,5'-tetraphenylbiimidazole, 2,2'-bis(o-chlorophenyl)-4,4',5,5'-tetra(m-methoxyphenyl)biimidazole, 2,2'-bis(o-,o'-dichlorophenyl)-4,4',5,5'-tetraphenylbimidazole, 2,2'-bis(o-nitrophenyl)-4,4',5,5'-tetraphenylbiimidazole, 2,2'-bis(o-methylphenyl)-4,4',5,5'-tetraphenylbiimidazole, and 2,2'-bis (o-trifluorophenyl)-4,4',5,5'-tetraphenylbiimidazole.

Examples of the ketoxime ester compounds (v) include 3-benzoyloxyiminobutan-2-one, 3-acetoxyiminobutan-2-one, 3-propionyloxyiminobutan-2-one, 2-acetoxyiminopentane-3-one, 2-acetoxyimino-1-phenylpropan-1-one, 2-benzoyloxyimino-1-phenylpropan-1-one, 3-p-toluenesulfonyloxyiminobutan-2-one, and 2-ethoxycarbonyloxyimino-1-phenylpropan-1-one.

Examples of the borate compounds (vi) include the compounds described in U.S. Pat. Nos. 3,567,453 and 4,343,891, and EP Patent No. 109,772 and 109,773.

Examples of the azinium compounds (vii) include the compounds containing an N—O bond described in JP-A Nos. 63-138345, 63-142345, 63-142346, and 63-143537, and JP-B No. 46-42363.

Examples of the metallocene compounds (viii) include the titanocene compounds described in JP-A Nos. 59-152396, 61-151197, 63-41484, 2-249, and 2-4705 and the iron-allene complexes described in JP-A Nos. 1-304453 and 1-152109.

Examples of the titanocene compounds include di-cyclopentadienyl-Ti-dichloride, di-cyclopentadienyl-Ti-bisphenyl, di-cyclopentadienyl-Ti-bis-2,3,4,5,6-pentafluorophen-1-yl, di-cyclopentadienyl-Ti-bis-2,3,5,6-tetrafluorophen-1-yl, di-cyclopentadienyl-Ti-bis-2,4,6-trifluorophen-1-yl, di-cyclopentadienyl-Ti-2,6-difluorophen-1-yl, di-cyclopentadienyl-Ti-bis-2,4-difluorophen-1-yl, di-methylcyclopentadienyl-Ti-bis-2,3,4,5,6-pentafluorophen-1-yl, di-methylcyclopentadienyl-Ti-bis-2,3,5,6-tetrafluorophen-1-yl, di-methylcyclopentadienyl-Ti-bis-2,4-difluorophen-1-yl, bis (cyclopentadienyl)-bis(2,6-difluoro-3-(pyr-1-yl)phenyl)titanium, bis(cyclopentadienyl) bis[2,6-difluoro-3-(methyl sulfonamide)phenyl]titanium, and bis(cyclopentadienyl) bis[2, 6-difluoro-3-(N-butylbiaroyl-amino)phenyl)titanium.

Examples of the active ester compounds (ix) include nitrobenzyl ester compounds described in EP Patent Nos. 0290750, 046083, 156153, 271851, and 0388343, U.S. Pat. Nos. 3,901,710 and 4,181,531, and JP-A Nos. 60-198538 and 53-133022; iminosulfonate compounds described in EP Patent Nos. 0199672, 84515, 199672, 044115, and 0101122, U.S. Pat. Nos. 4,618,564, 4,371,605, and 4,431,774, and JP-A Nos. 64-18143, 2-245756 and 4-365048; and compounds described in JP-B Nos. 62-6223 and 63-14340, and JP-A No. 59-174831.

Examples of the compounds (x) containing a carbon-halogen bond include compounds described in Wakabayashi et al., Bull. Chem. Soc. Japan, 42, 2924 (1969), compounds described in British Patent No. 1388492, compounds described in JP-A No. 53-133428, and compounds described in German Patent No. 3337024.

Further examples of the compounds containing a carbon-halogen bond include compounds described in F. C. Schaefer et al., J. Org. Chem. 29, 1527 (1964), compounds described in JP-A No. 62-58241, compounds described in JP-A No. 5-281728, compounds described in German Patent No. 2641100, compounds described in German Patent No. 3333450, compounds described in German Patent No. 3021590, and compounds described in German Patent No. 3021599.

Preferable specific examples of the compounds represented by (i) to (x) described above are shown below.

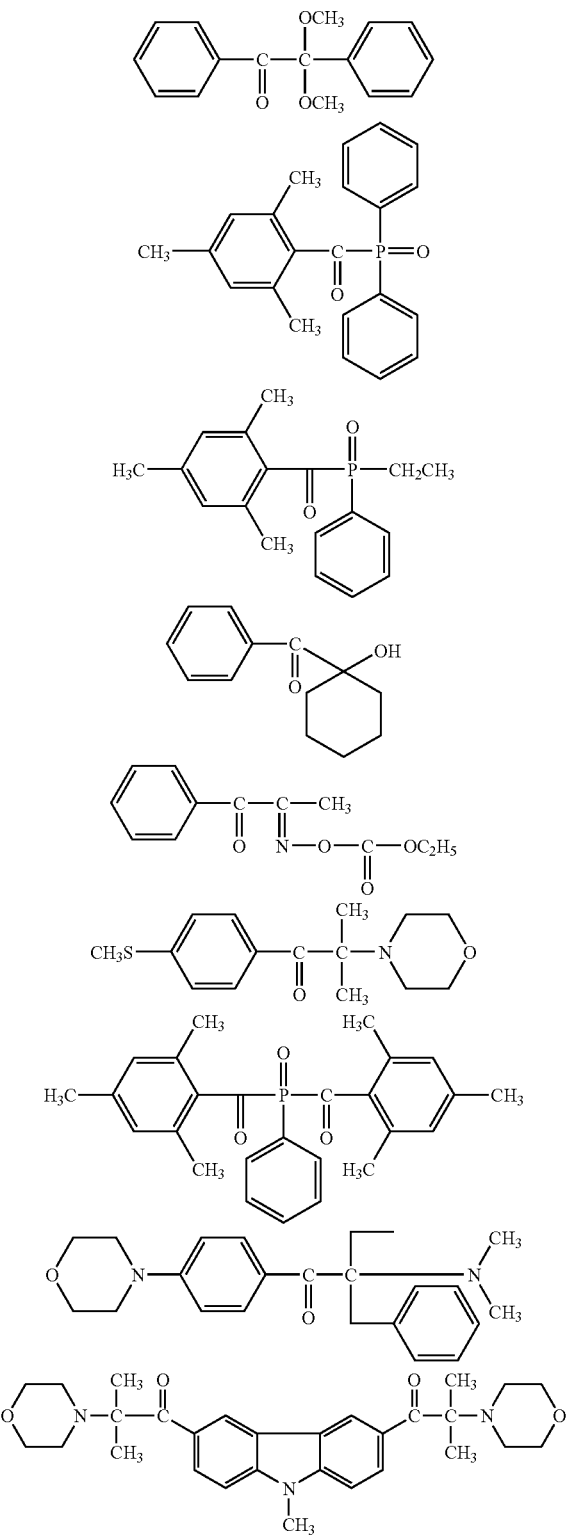

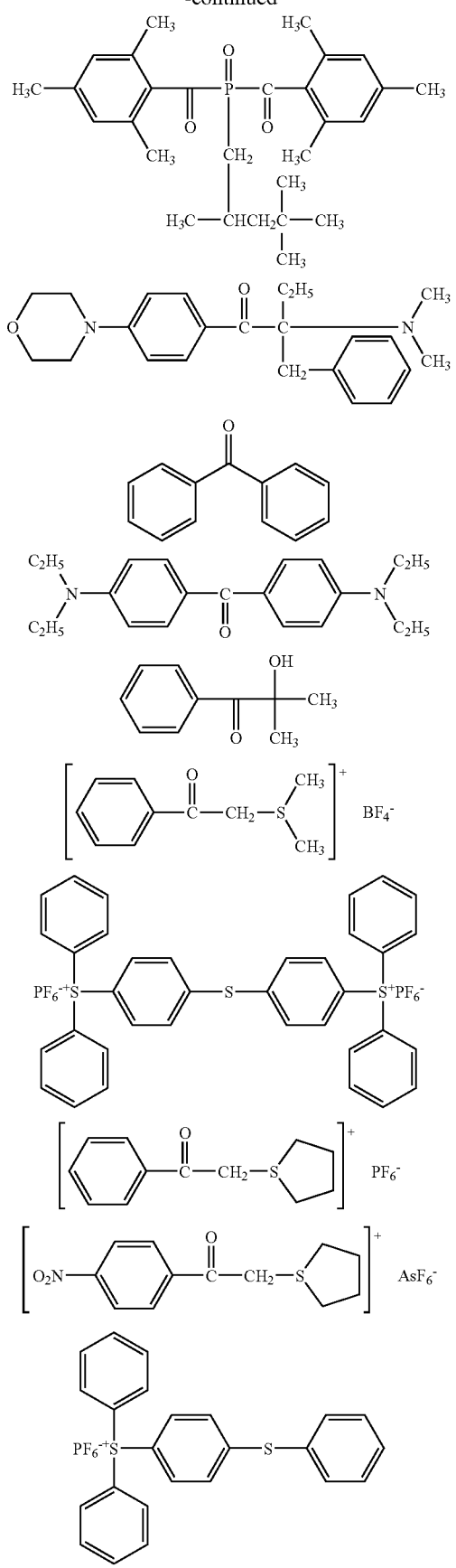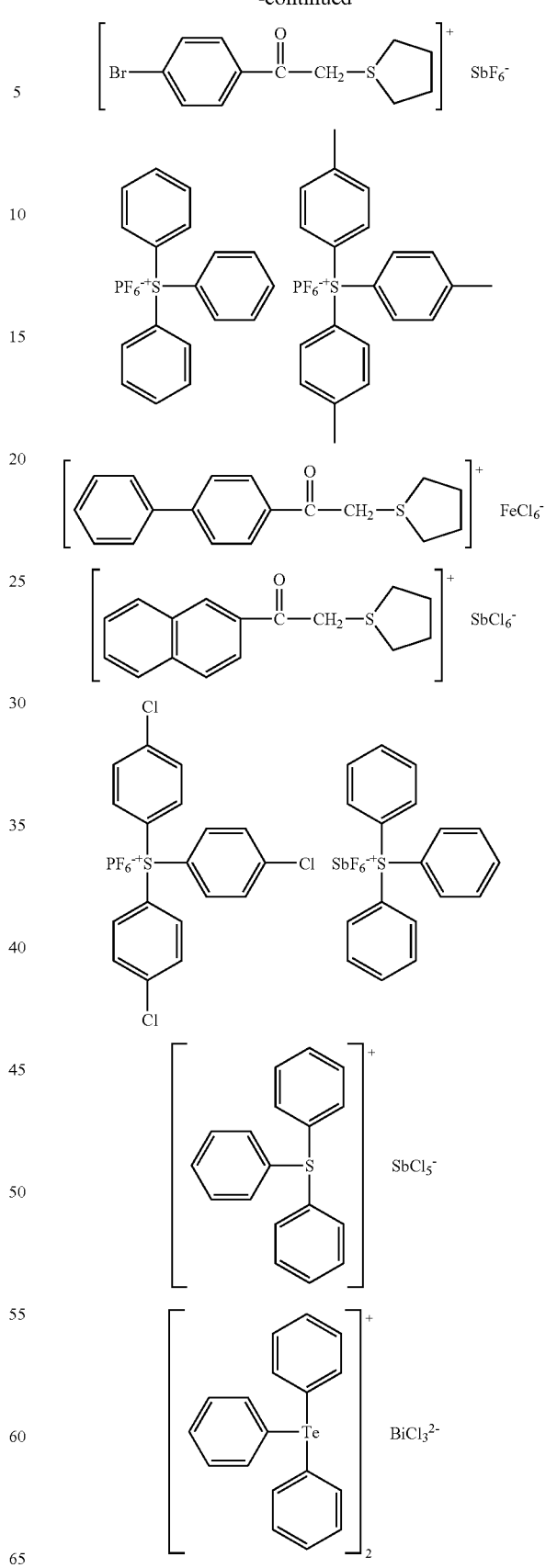

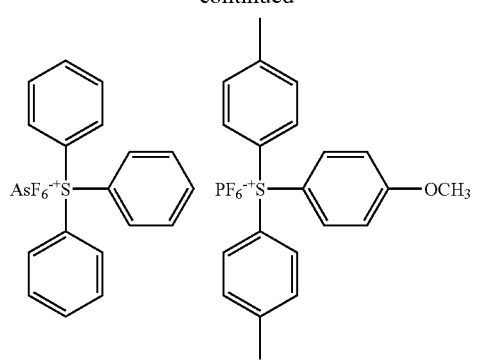
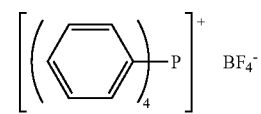
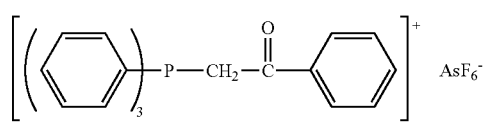
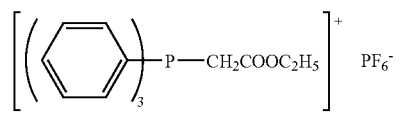
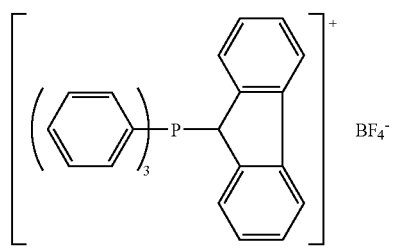
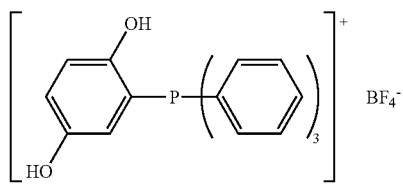
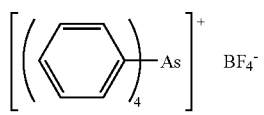
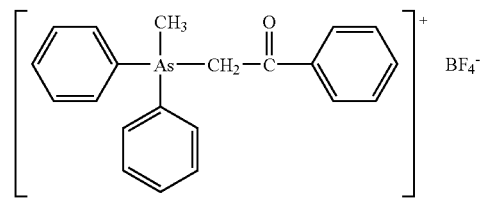
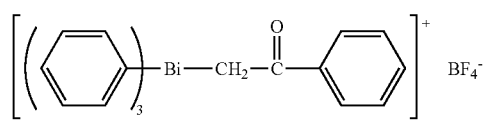
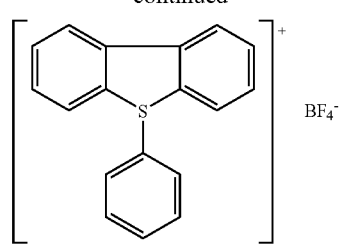
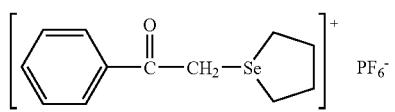
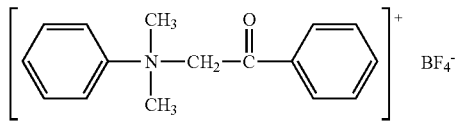
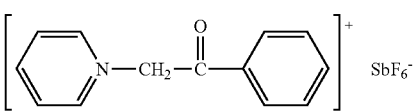
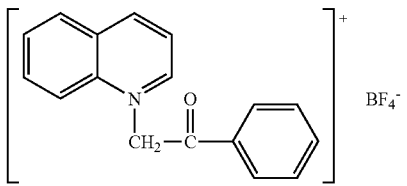
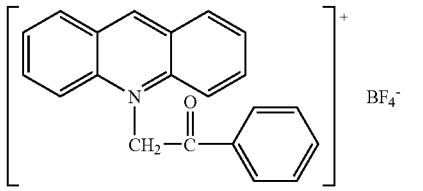
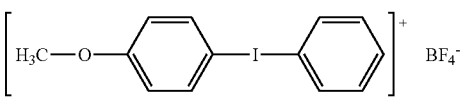
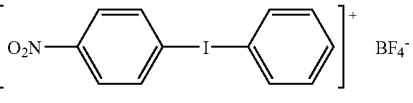
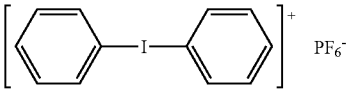
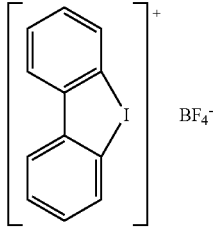
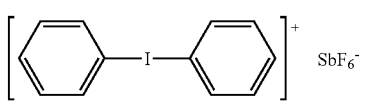

31
-continued
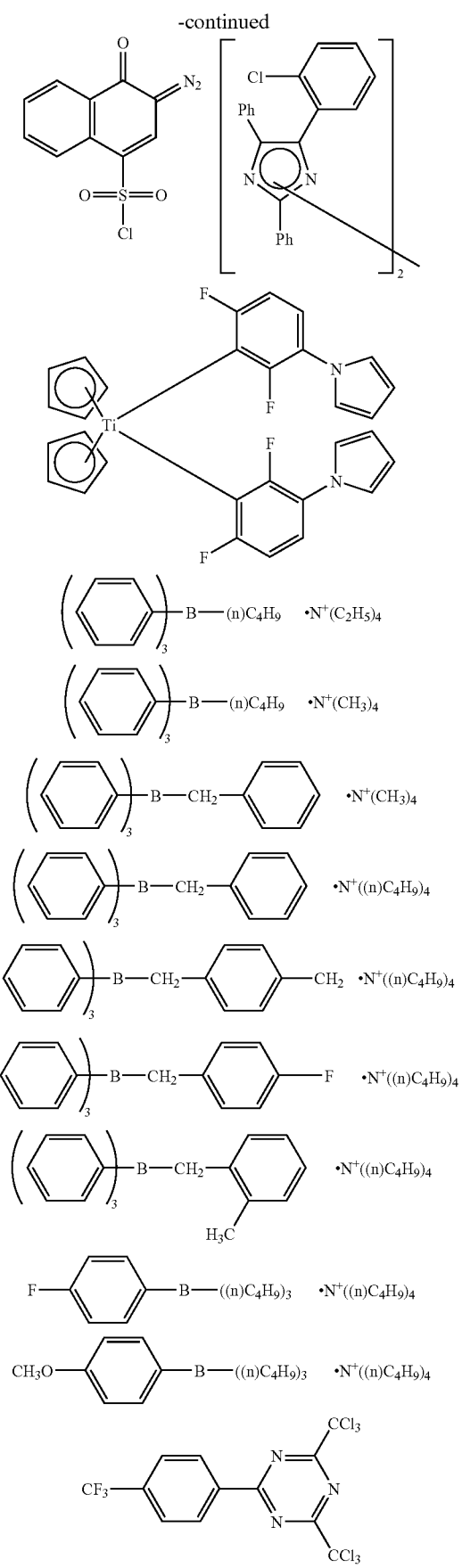
32
-continued
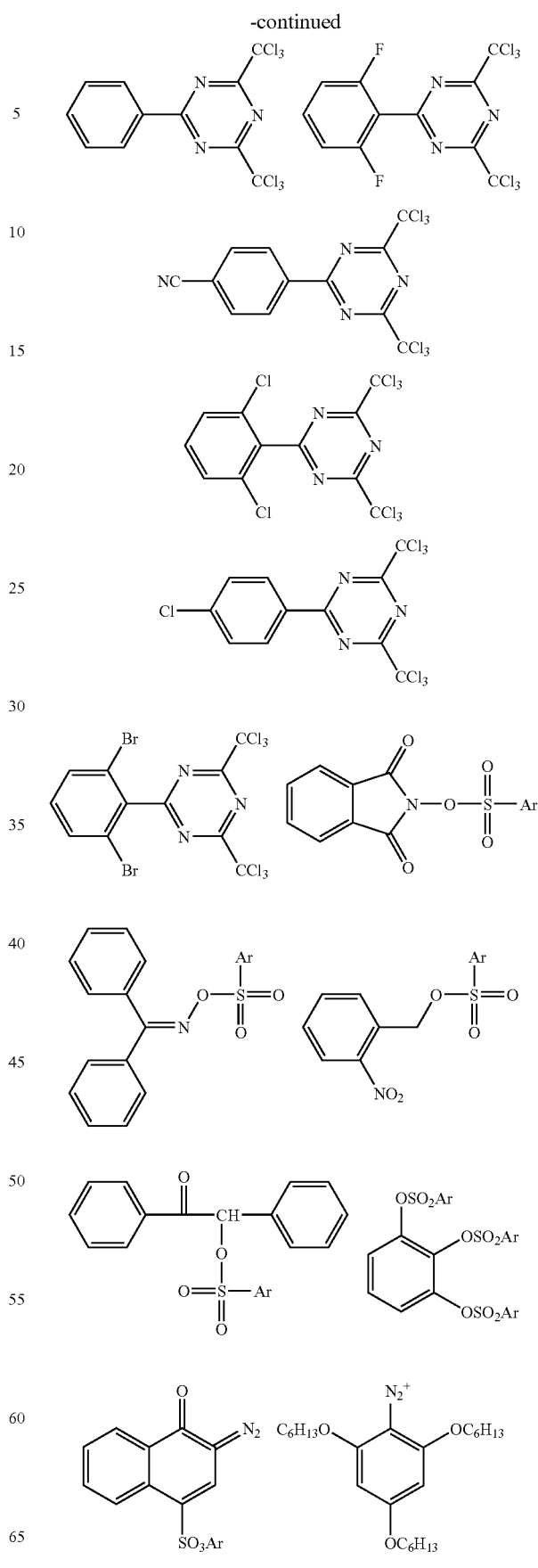

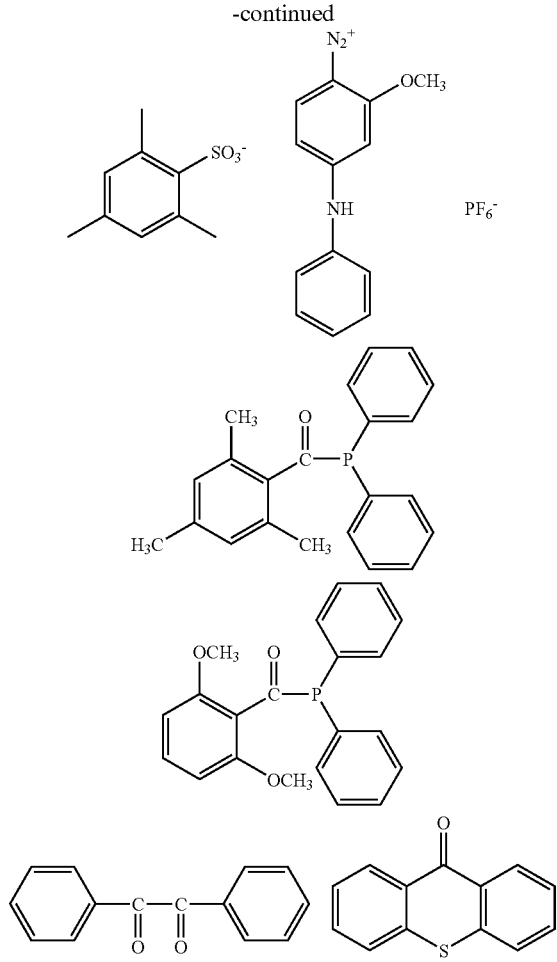

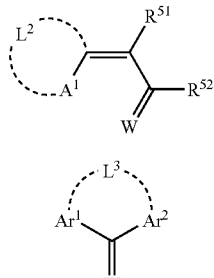

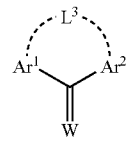

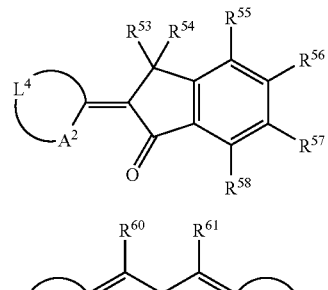

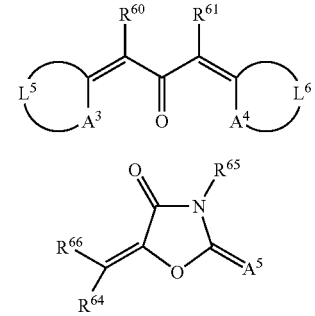

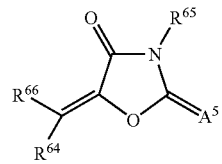

Only one photopolymerization initiator may be used, or two or more photopolymerization initiators may be used in combination. The content of the photopolymerization initiator in the ink composition is preferably 0.1% by mass to 20% by mass, more preferably 0.5% by mass to 10% by mass, most preferably 1% by mass to 7% by mass, based on the total solid content in the ink composition.

<Other Component>

—Sensitizing Dye—

In the present invention, a sensitizing dye may be added for the purpose of improving the sensitivity of the photopolymerization initiator. For the sensitizing dye, those are preferable that belong to the following compound classes and have absorption wavelengths in the range of 350 nm to 450 nm.

Examples of the sensitizing dye include multinuclear aromatics (e.g., pyrene, perylene, triphenylene, and anthracene), xanthenes (e.g., fluorescein, eosin, erythrosine, rhodamine B, and Rose Bengal), cyanines (e.g., thiacarbocyanine and oxacarbocyanine), merocyanines (e.g., merocyanine and carbomerocyanine), thiazines (e.g., thionine, methylene blue, and toluidine blue), acridines (e.g., acridine orange, chloroflavin, and acryflavin), anthraquinones (e.g., anthraquinone), squaliums (e.g., squalium), and coumarins (e.g., 7-diethylamino-4-methyl coumarin).

For the sensitizing dye, compounds represented by the following formulae (IX) to (XIII) are more preferable.

In formula (IX), $A^1$ represents a sulfur atom or —$NR^{50}$—, $R^{50}$ represents an alkyl group or an aryl group, $L^2$ represents a nonmetallic atomic group which, together with $A^1$ and the carbon atom adjacent thereto, forms a basic nucleus of a dye, $R^{51}$ and $R^{52}$ each independently represent a hydrogen atom or a monovalent nonmetallic atomic group, $R^{51}$ and $R^{52}$ may be bound to each other to form an acidic nucleus of a dye, and W represents an oxygen atom or a sulfur atom.

In formula (X), $Ar^1$ and $Ar^2$ each independently represent an aryl group, and are bound to each other via a linkage -$L^3$- which represents —O— or —S—. W has the same definition as in formula (IX).

In formula (XI), $A^2$ represents a sulfur atom or $NR^{59}$, $L^4$ represents a nonmetallic atomic group which, together with $A^2$ and the carbon atom adjacent thereto, forms a basic nucleus of a dye, $R^{53}$, $R^{54}$, $R^{55}$, $R^{56}$, $R^{57}$ and $R^{58}$ each independently represent a monovalent nonmetallic atomic group, and $R^{59}$ represents an alkyl group or an aryl group.

In formula (XII), $A^3$ and $A^4$ each independently represent —S— or —$NR^{62}$— or —$NR^{63}$—. $R^{62}$ and $R^{63}$ each independently represent a substituted or unsubstituted alkyl group or a substituted or unsubstituted aryl group. $L^5$ represents a nonmetallic atomic group which, together with $A^3$ and the carbon atom adjacent thereto, forms a basic nucleus of a dye. $L^6$ represents a nonmetallic atomic group which, together with $A^4$ and the carbon atom adjacent thereto, forms a basic nucleus of a dye. $R^{60}$ and $R^{61}$ each independently represent a hydrogen atom or a monovalent nonmetallic atomic group, or $R^{60}$ and $R^{61}$ are bound to each other to form an aliphatic or aromatic ring.

In formula (XIII), $R^{66}$ represents an optionally substituted aromatic cycle or heterocycle, $A^5$ represents an oxygen atom, a sulfur atom, or —NR$^{67}$—. R$^{64}$, R$^{65}$, and R$^{67}$ each independently represent a hydrogen atom or a monovalent nonmetallic atomic group. R$^{67}$ and R$^{64}$ may be bonded to each other to form an aliphatic or aromatic ring. R$^{65}$ and R$^{67}$ may be bonded to each other to form an aliphatic or aromatic ring.

Preferable specific examples of the compounds represented by formulae (IX) to (XIII) include exemplary compounds (A-1) to (A-24) shown below.

(A-1)
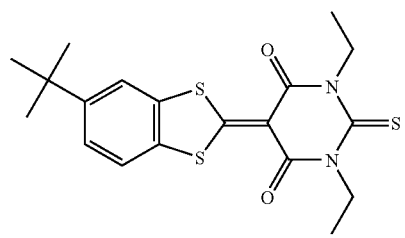

(A-2)
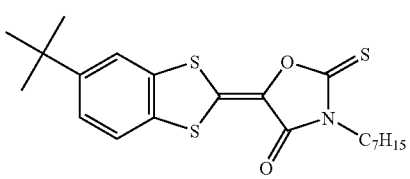

(A-3)
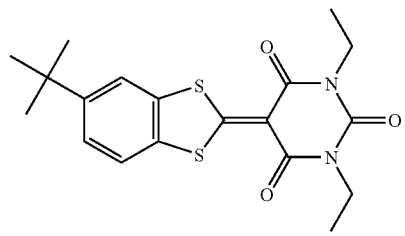

(A-4)
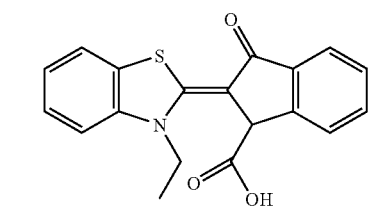

(A-5)
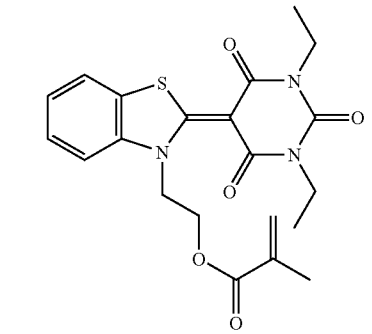

(A-6)
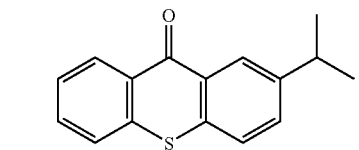

(A-7)
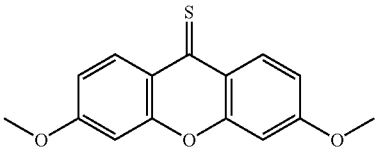

(A-8)
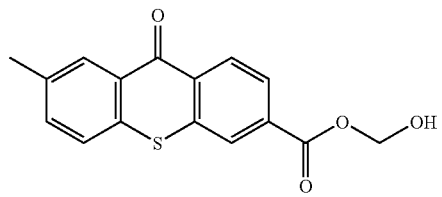

(A-9)
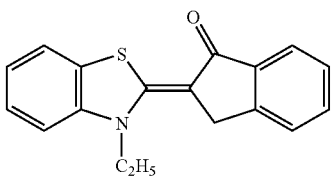

(A-10)
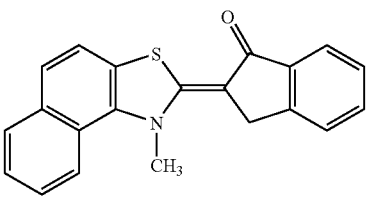

(A-11)
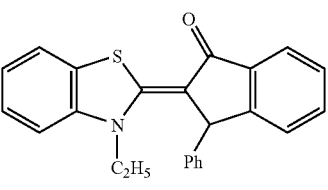

(A-12)
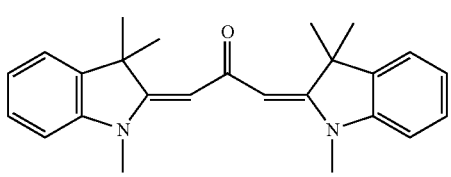

(A-13)
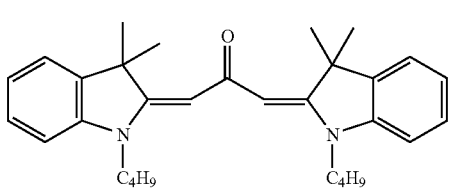

(A-14)
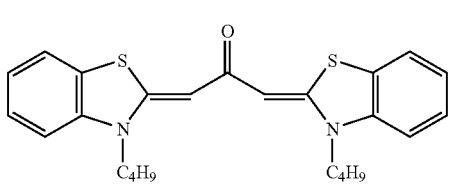

(A-15) 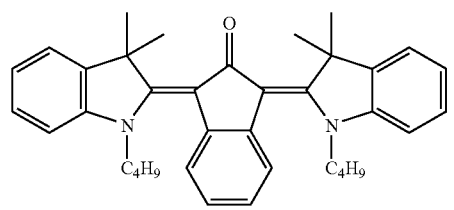

(A-16) 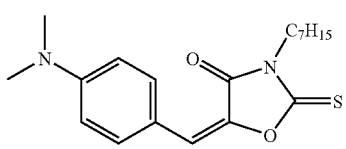

(A-17) 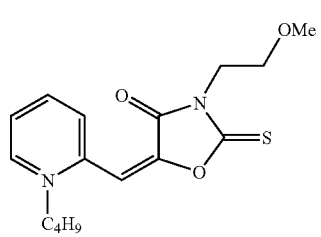

(A-18) 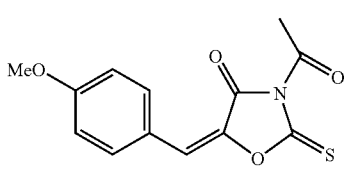

(A-19) 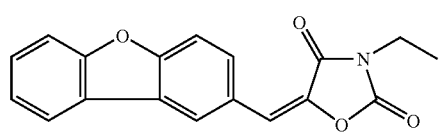

(A-20) 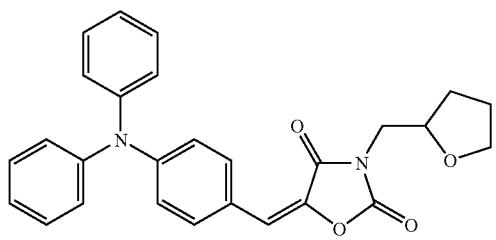

(A-21) 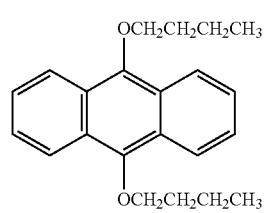

(A-22) 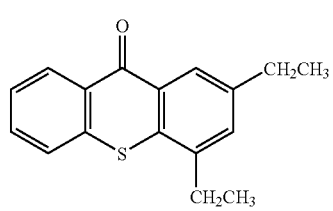

(A-23) 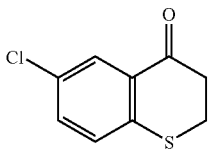

(A-24) 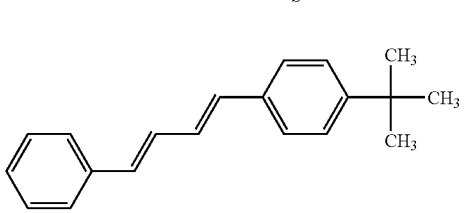

—Cosensitizer—

To the ink composition of the present invention, a known compound that has a function of further improving the sensitivity or suppressing the inhibition of polymerization by oxygen may be added as a cosensitizer.

Examples of the cosensitizer include the amines described, for example, in M. R. Sander et al., "Journal of Polymer Society" 10, p. 3173, (1972), JP-B No. 44-20189, JP-A Nos. 51-82102, 52-134692, 59-138205, 60-84305, 62-18537, and 64-33104 and Research Disclosure 33825; and specific examples thereof include triethanolamine, ethyl p-dimethylaminobenzoate, p-formyldimethylaniline, and p-methylthiodimethylaniline.

Other examples of the cosensitizer include thiols and sulfides, for example, the thiol compounds described in JP-A No. 53-702, JP-B No. 55-500806, and JP-A No. 5-142772, and the disulfide compounds described in JP-A No. 56-75643; and specific examples thereof include 2-mercaptobenzothiazole, 2-mercaptobenzoxazole, 2-mercaptobenzimidazole, 2-mercapto-4(3H)-quinazoline, and b-mercaptonaphthalene.

Yet other examples of the cosensitizer include amino acid compounds (e.g., N-phenylglycine), the organic metal compounds described in JP-B No. 4842965 (e.g., tributyltin acetate), the hydrogen donors described in JP-B No. 55-34414, the sulfur compounds described in JP-A No. 6-308727 (e.g., trithiane), the phosphorus compounds described in JP-A No. 6-250387 (e.g., diethyl phosphite), and the Si—H and Ge—H compounds described in JP-A No. 6-191605.

In addition to the essential components, the other polymerizable compound (a) and (b) pigment, a preferable optional component, the polymerization initiator (c), and the sensitizing dye and cosensitizer that can be used together with the polymerization initiator (c), the ink composition according to the present invention may further contain various additives according to the purpose. For example, an ultraviolet absorbent may be added to the ink composition according to the present invention, for the improvement in the weather resistance of the obtained image and prevention of the discoloration of the image. In addition, an antioxidant may be added to improve the stability of the ink composition.

Other usable additives include: an organic or metal-complex-based anti-fading agent; a conductive salt for the control of the ejection properties, such as potassium thiocyanate, lithium nitrate, ammonium thiocyanate, or dimethylamine hydrochloride salt; and a trace amount of an organic solvent for the improvement of the adhesion to the recording medium.

The ink composition according to the present invention may further contain a polymer compound selected from various polymer compounds for the purpose of the adjustment of the film physical properties. Examples of polymer compounds include acrylic polymers, polyvinylbutyral resins, polyurethane resins, polyamide resins, polyester resins, epoxy resins, phenol resins, polycarbonate resins, polyvinylbutyral resins, polyvinylformal resins, shellac, vinyl resins, acrylic resins, rubber resin, waxes, and other natural resins. Two or more polymer compounds may be used simultaneously.

One or more substances selected from nonionic surfactants, cationic surfactants, and organic fluorocompounds may be added to the ink composition of the present invention in order to control the liquid properties.

The ink composition of the present invention may contain other additives as necessary, for example, leveling additives, matting agents, waxes for controlling the film properties, and tackifiers, which do not inhibit polymerization, for improving the adhesion to recording media such as polyolefin and PET.

The ink composition of the present invention has a viscosity of preferably 30 mPa·s or less and more preferably 20 mPa·s or less at the temperature of injection taking injection ability into account. It is preferable to control and determine the ratio of the composition properly such that the viscosity of the ink composition falls in the above range. It is to be noted that the viscosity of the ink at 25° C. (room temperature) is 200 mPa·s or less and preferably 100 mPa·s. By setting the viscosity high at room temperature, even if a porous recording medium is used, it is possible to prevent permeation of ink into the recording medium, reduce the amount of an uncured monomer, and decrease odors, and further, blurring of dots when ink droplets are impacted can be suppressed, resulting in improved image quality. When the viscosity of the ink at 25° C. is higher than 200 mPa·s, a problem arises concerning the delivery of the ink liquid.

The surface tension of the ink composition according to the present invention is preferably 20 mN/m to 30 mN/m and more preferably 23 mN/m to 28 mN/m. When the ink is used for recording on various recording media such as polyolefin, PET, coated paper, and non-coated paper, the surface tension is preferably 20 mN/m or more in view of the prevention of bleeding and penetration, and 30 mN/m or less in view of the wettability.

The ink composition of the present invention prepared in this manner is suitably used as an inkjet recording ink. The recording can be conducted by applying the ink composition on a recording medium by printing using an inkjet printer, and then irradiating the applied ink composition with a radiation ray to cure the composition.

In the printed articles obtained by the ink, the image portion has been cured by irradiation with radiation rays such as ultraviolet rays and the printed articles are therefore superior in the strength of the image portion. Therefore, the ink composition of the present invention may be used in various applications such as the formation of the ink receptor layer (image portion) of a planographic printing plate, besides image formation using ink.

(Inkjet Recording Method and Inkjet Recording Apparatus)

Next, an inkjet recording method and an inkjet recording apparatus, which are suitably adopted in the present invention, will be described below.

In the inkjet recording method, it is preferable to eject the ink composition after the viscosity of ink composition is lowered to 30 mPa·s or less by heating to 40° C. to 80° C., and in this manner, it is possible to realize highly stable ejection. Radiation-curable ink compositions are usually more viscous than aqueous inks. Thus, generally, fluctuation in the viscosity of radiation-curable ink compositions caused by the fluctuation in temperature during printing is larger. The fluctuation in the viscosity of ink composition exerts significant influences on the droplet size and the droplet ejection speed, causing deterioration in image quality, and thus, it is necessary to keep the temperature of the ink composition as constant as possible during printing. It is preferable to control the ink composition temperature within 5° C. from the set temperature, more preferably 2° C. from the set temperature, and most preferably 1° C. from the set temperature.

The inkjet recording apparatus may have an ink-temperature stabilizing device. The ink-temperature stabilizing device maintains a constant temperature of the ink composition in all the piping systems and members from the ink tank (from the intermediate tank if such an intermediate tank is present) to the ejection face on the nozzles.

The temperature can be controlled by any method without limitation. For example, it is preferable to control heating conditions according to the flow rate of the ink composition and the environmental temperature based on the information supplied from plural temperature sensors provided to the respective pipes. The heat unit to be heated is preferably insulated thermally such that the unit is not affected by the environmental temperature. Preferably, the heat unit is thermally insulated from the other portions, and the total heat capacity of the heating unit is small, whereby the printer starting-up time required for heating is shortened and the heat energy loss is reduced.

An active radiation-curable ink composition can be obtained by adding the photopolymerization initiator as the polymerization initiator (c) to the ink composition of the present invention.

Conditions of the irradiation of the ink composition with an active radiation ray will be described below. A basic method of the irradiation is disclosed in JP-A No. 60-132767. Specifically, light sources are disposed at both sides of a head unit, and the head unit and the light sources are scanned in the shuttle mode. The ink composition is irradiated with the active radiation ray after a predetermined period from the deposition of the ink composition on the recording medium. The ink composition is cured using another light source that is not driven. Specifically, WO 99/54415 discloses an irradiation method comprising using an optical fiber and an irradiation method comprising irradiating the recording area with UV rays by directing a collimated rays to a mirror surface on the sidewall of head unit. These irradiation methods may be used in the present invention.

Further, in the present invention, it is desirable to heat the ink composition to a predetermined temperature and adjust the period between the deposition of the ink composition on the recording medium and the irradiation with radiation rays to 0.01 second to 0.5 second, preferably 0.01 second to 0.3 second, and more preferably 0.01 second to 0.15 second. It becomes possible to prevent bleeding of the deposited ink composition before curing, by shortening the period between the deposition of the ink composition on the recording medium and the irradiation with radiation rays to such an extremely short period. Further, even when the recording medium is porous, the ink composition is irradiated before penetrating deep into the recording medium. Thus, the amount of the remaining unreacted monomer is reduced and consequently the odor is also reduced. The combination of the inkjet recording method and the ink composition of the present invention provides significant synergy effects. In particular when the viscosity of the ink composition at 25° C. is 200 mPa·s or less, significant effects can be obtained. By employing such an inkjet recording method, it is possible to maintain the dot diameter of the deposited ink composition constant and obtain an image with improved quality, on any of various recording media different in surface wettability. In order to obtain a color image, it is preferable to form images in the order from a color lower in lightness. When an ink of lower lightness is deposited, the radiation rays are unlikely to reach the inks located at the bottom; therefore, curing sensitivity and improvement in adhesiveness are likely to be deteriorated, and the residual monomer is likely to be increased to cause odor. Although it is possible to eject inks of all colors and then conduct the irradiation at the same time, it is preferable to irradiate the image with radiation rays after each color ink is deposited, in view of the acceleration of curing.

The inkjet recording apparatus used in the present invention is not particularly limited, and a commercial inkjet recording apparatus can be used. In other words, in the present invention, the recording on recording media (printed articles) can be conducted by a commercial inkjet recording apparatus.

In the preferable ejecting conditions described above, although the ink composition of the present invention is repeatedly heated and cooled, reduction in pigment dispersibility is avoided, excellent coloring property is achieved over a long period, and the deterioration of the ejection property caused by the aggregation of the pigment is also avoided owing to the function of the specific polymer that contains a copolymer unit derived from the monomers represented by the formula (1) to (3) even when the ink composition is stored under such temperature conditions.

(Recording Medium (Printed Articles))

The recording medium to which the ink composition according to the present invention is applicable is not particularly limited, and examples thereof include ordinary papers such as non-coated paper, coated paper, and corrugated paper, various non-absorptive resin materials for use in so-called soft packaging, and resin films thereof in the film shape. Examples of such various plastic films include PET film, OPS film, OPP film, ONy film, PVC film, PE film, and TAC film. Examples of other plastics usable as the material of the recording medium include polycarbonate, acrylic resins, ABS, polyacetal, PVA, and rubbers. In addition, metals and glasses are also usable as the recording media. Recording media having a large area may also be used.

The ink composition of the present invention is used to print on a recording medium by an inkjet printer and then, preferably, the ink composition applied by printing is irradiated with an active radiation ray and cured, whereby the printed articles of the present invention can be obtained. The printed article of the present invention has a high quality image superior in coloring property and sharpness and is also superior in the weather resistance of the image because the ink used for image formation contains fine pigment particles uniformly and stably in a dispersed state. The ink composition of the invention is therefore applied in a wide range of fields.

EXAMPLES

The present invention will be explained in more detail by way of Examples, which are not intended to limit the present invention.

Example 1

Synthesis of Polymerizable Compound and Polymer Thereof

—Synthesis of M-1—

355.0 g of 1,8-naphthalimide was dissolved in 1,500 mL of N-methylpyrrolidone, and 0.57 g of nitrobenzene was added at 25° C. 301.4 g of diazabicycloundecene (DBU) was added dropwise to the mixture. After stirring for 30 minutes, 412.1 g of chloromethylstyrene was added dropwise to the mixture, which was then heated at 60° C. with stirring for 4 hours. 2.7 L of isopropanol and 0.9 L of distilled water were added to this reaction solution and stirred while cooling to 5° C. The resulting precipitates were separated by filtration and washed with 1.2 L of isopropanol to obtain 544.0 g of polymerizable compound M-1.

From NMR data shown below, the compound obtained was confirmed to be polymerizable compound M-1.

1H-NMR (300 MHz, CDCl$_3$, δ): 8.61 (d, 2H), 8.21 (d, 2H), 7.75 (t, 2H), 7.25-7.60 (m, 4H), 6.66 (m, 1H), 5.73 (dd, 1H), 5.38 (s, 2H), 5.20 (dd, 1H).

—Synthesis of M-3—

19.7 g of 1,8-naphthalimide was dissolved in 100 mL of N-methylpyrrolidone, 11.1 g of triethylamine was added and stirred. 20.2 g of 4-vinylbenzene sulfonyl chloride was added dropwise to the mixture and stirred for 2 hours. 500 mL of distilled water was added to this reaction solution and stirred while cooling to 5° C. The resulting precipitates were separated by filtration and washed with methanol to obtain 20.0 g of polymerizable compound M-3.

From NMR data shown below, the compound obtained was confirmed to be polymerizable compound M-3.

1H-NMR (300 MHz, CDCl$_3$, δ): 8.61 (d, 2H), 8.21 (d, 2H), 8.01 (d, 2H), 7.75 (t, 2H), 7.60 (d, 2H), 6.76 (m, 1H), 5.93 (dd, 1H), 5.58 (dd, 1H), 5.40 (d, 2H).

—Synthesis of Graft Copolymer 1—

2.0 g of M-1, 18.0 g of polymethyl methacrylate having a methacryloyl group at one terminal (AA-6, manufactured by Toagosei Co., Ltd.), and 20 g of methyl ethyl ketone were introduced into a three-neck flask in which the atmosphere was substituted with nitrogen, stirred with a stirrer (Three-one Motor, manufactured by Shinto Scientific Co., Ltd.) and heated to raise the temperature to 78° C. with nitrogen flowing in the flask. 27 mg of 2,2-azobis(2,4-dimethylvaleronitrile) (V-65, manufactured by Wako Pure Chemical Industries, Ltd.) was added to the above solution and heated at 78° C. with stirring for 2 hours. After 2 hours, 27 mg of V-65 was further added and heated with stirring for 3 hours. The resulting reaction solution was poured into 1,000 mL of hexane with stirring, and the precipitates produced were heated and dried to obtain a graft copolymer 1 (the above listed graft copolymer 1: A copolymer of the monomer represented by M-1, and polymethylmethacrylate having a methacryloyl group at its terminal).

The weight average molecular mass (polystyrene standard) of the graft copolymer 1, determined by GPC, was 31,500. Thus, it was confirmed that polymer was obtained.

For GPC, Shodex GPC KF-804 (Showa Denko K.K.) was used as a column, and THF was used as an eluent. Measurement was performed at a flow rate of 0.8 mL/min and a column temperature of 40° C., and refractive index (RI) detection was used.

—Synthesis of Graft Copolymer 2—

2.0 g of M-1, 2.0 g of 3-(N,N-dimethylaminopropyl acrylamide), 16.0 g of polymethyl methacrylate having a methacryloyl group at one terminal (AA-6, manufactured by Toagosei Co., Ltd.), and 20 g of methyl ethyl ketone were introduced into a three-neck flask in which the atmosphere was substituted with nitrogen, stirred with a stirrer (Three-one Motor, manufactured by Shinto Scientific Co., Ltd.) and heated to raise the temperature to 78° C. with nitrogen flowing in the flask. 27 mg of 2,2-azobis(2,4-dimethylvaleronitrile) (V-65, manufactured by Wako Pure Chemical Industries, Ltd.) was added to the above solution and heated at 78° C. with stirring for 2 hours. After 2 hours, 27 mg of V-65 was further added and heated with stirring for 3 hours. The resulting reaction solution was poured into 1,000 mL of hexane with stirring, and the precipitates produced were heated and dried to obtain a graft copolymer 2 (the above listed graft copolymer 8: A copolymer of the monomer represented by M-1,3-(N,N-dimethylamino)propyl acrylamide, and polymethylmethacrylate having a methacryloyl group at its terminal).

The weight average molecular mass (polystyrene standard) of the graft copolymer 2, determined by GPC, was 56,600. Thus, it was confirmed that polymer was obtained.

—Synthesis of Graft Copolymer 3—

A graft copolymer 3 (the above listed graft copolymer 2: A copolymer of the monomer represented by M-1, and polyethylene glycol mono(meth)acrylate) was obtained in the same way as in the synthetic example of graft copolymer 1 except that the "polymethyl methacrylate having a methacryloyl group at one terminal" of the synthetic example of graft copolymer 1 was changed to "methoxypolyethylene glycol methacrylate" (NK ESTER M-230G, manufactured by Shin-Nakamura Chemical Co., Ltd.).

The weight average molecular mass (polystyrene standard) of the graft copolymer 3, determined by GPC, was 24,500. Thus, it was confirmed that polymer was obtained.

—Synthesis of Graft Copolymer 4—

A graft copolymer 4 (the above listed graft copolymer 4: A copolymer of the monomer represented by M-1, and polybutyl acrylate having a methacryloyl group at its terminal) was obtained in the same way as in the synthetic example of graft copolymer 1 except that the "polymethyl methacrylate having a methacryloyl group at one terminal" of the synthetic example of graft copolymer 1 was changed to "polybutyl acrylate having a methacryloyl group at one terminal" (AB-6, manufactured by Toagosei Co., Ltd.).

The weight average molecular mass (polystyrene standard) of the graft copolymer 4, determined by GPC, was 28,800. Thus, it was confirmed that polymer was obtained.

—Synthesis of Graft Copolymer 5—

A graft copolymer 5 (the above listed graft copolymer 5: A copolymer of the monomer represented by M-3, and polymethylmethacrylate having a methacryloyl group at its terminal) was obtained in the same way as in the synthetic example of graft copolymer 1 except that M-1 of the synthetic example of graft copolymer 1 was changed to M-3.

The weight average molecular mass (polystyrene standard) of the graft copolymer 5, determined by GPC, was 18,700. Thus, it was confirmed that polymer was obtained.

—Synthesis of Graft Copolymer 6—

A graft copolymer 6 (the above listed graft copolymer 16: A copolymer of the monomer represented by M-1, methacrylic acid, and polymethylmethacrylate having a methacryloyl group at its terminal) was obtained in the same way as in the synthetic example of graft copolymer 2 except that the "3-(N,N-dimethylaminopropyl acrylamide)" of the synthetic example of graft copolymer 2 was changed to "methacrylic acid".

The weight average molecular mass (polystyrene standard) of the graft copolymer 6, determined by GPC, was 19,800. Thus, it was confirmed that polymer was obtained.

Graft copolymer 1 (the graft copolymer 1 listed above: copolymer of the monomer, represented by M-1, and polymethylmethacrylate having a methacryloyl group at its terminal) was dissolved in other polymerizable compounds (a), (i) and (ii), and the mixture was placed together with a pigment (b) in a Motor Mill M50 (manufactured by Eiger Co., Ltd.) to disperse the mixture at a peripheral speed of 9 m/s for 6 hours by using zirconia beads 0.65 mm in diameter, thereby obtaining a reaction mixture of active energy ray-curable ink. Then, the polymerization initiator (c) was added to the reaction mixture and mixed mildly, followed by filtration under pressure using a membrane filter to obtain an active energy ray-curable type inkjet ink of Example 1. The amounts of graft copolymer 1, other polymerizable compounds (a), (i) and (ii), pigment (b), and polymerization initiator (c) added are shown below.

| | |
|---|---|
| Graft copolymer 1 | 1.5 g |
| (a) Other polymerizable compound: | |
| (i) propoxylated neopentyl glycol diacrylate (NPGPODA, manufactured by Sartomer Company, Inc.) | 60.0 g |
| (ii) caprolactone-modified dipentaerythritol hexaacrylate (DPCA-60, manufactured by Nippon Kayaku Co., Ltd.) | 27.5 g |
| (b) Pigment: quinacridone base pigment PV-19 | 5.0 g |
| (c) Polymerization initiator: acylphosphine oxide compound (LucirinTPO-L, manufactured by BASF) | 5.0 g |

Examples 2 to 6

Active energy ray-curable type inkjet inks of Examples 2 to 6 were obtained in the same way as in Example 1 except that the graft copolymer 1 used in Example 1 was changed to the graft copolymers 2 to 6, respectively, prepared in the synthetic examples.

Comparative Example 1

An active energy ray-curable type inkjet ink of Comparative Example 1 was obtained in the same way as in Example 1 except that a commercially available pigment dispersant "SOLSPERSE 24000GR" (manufactured by Lubrizol Japan Ltd.) was used instead of the graft copolymer 1 used in Example 1.

Comparative Example 2

An active energy ray-curable type inkjet ink of Comparative Example 2 was obtained in the same way as in Example 1 except that a commercially available pigment dispersant "SOLSPERSE 32000" (manufactured by Lubrizol Japan Ltd.) was used instead of the graft copolymer 1 used in Example 1.

Example 7 and Comparative Examples 3 and 4

Inkjet ink compositions of Example 7 and Comparative Examples 3 and 4 were obtained in the same way as in Example 2 and Comparative Examples 1 and 2, respectively, except that the quinacridone base pigment PV-19 (b) was changed to PY-128.

Example 8 and Comparative Examples 5 and 6

Inkjet inks of Example 8 and Comparative Examples 5 and 6 were obtained in the same way as in Example 2 and Comparative Examples 1 and 2, respectively, except that the other polymerizable compound (a) and polymerization initiator (c) were changed to the following compounds.

| (a) Other polymerizable compound: | |
|---|---|
| (i) oxetane compound (OXT-221, manufactured by Toagosei Co., Ltd.) | 70.0 g |
| (ii) epoxy compound (Celoxide 3000, manufactured by Daicel Chemical Industries, Ltd.) | 17.5 g |
| (c) Polymerization initiator: triphenylsulfonium salt (UVI-6992, manufactured by Dow Chemical) | 5.0 g |

Example 9 and Comparative Examples 7 and 8

Inkjet inks of Example 9 and Comparative Examples 7 and 8 were obtained in the same way as in Example 8 and Comparative Examples 5 and 6, respectively, except that the quinacridone base pigment PV-19 was changed to a phthalocyanine-based pigment PB15:3.

Example 10

The polymer of the present invention shown below (graft copolymer 2) was dissolved in the following polymerizable compounds (a), and the mixture was placed together with the following pigment (b) in a Motor Mill M50 (manufactured by Eiger Co., Ltd.) to disperse the mixture at a peripheral speed of 5 m/s for 5 hours by using zirconia beads 0.65 mm in diameter, thereby obtaining a reaction mixture of active energy ray-curable ink. Then, a polymerization initiator (c) was added to the reaction mixture and mixed mildly, followed by filtration under pressure using a membrane filter to obtain an inkjet ink of Example 10.

| (b) Pigment [acetolone pigment PO-36 KENALAKE ORANGE HPRLO, manufactured by Albion Colours] | 4.0 g |
|---|---|
| Polymer of the present invention [graft copolymer 2 obtained in the synthetic example] | 1.2 g |
| (a) Polymerizable compound [propoxylated neopentyl glycol diacrylate (NPGPODA, manufactured by Sartomer Company, Inc. | 40.0 g |
| (a) Polymerizable compound [dipropylene glycol diacrylate (DPGDA, manufactured by DAICEL-CYTEC Company Ltd.] | 49.8 g |
| (c) Polymerization initiator [acylphosphine oxide compound (LucirinTPO-L: manufactured by BASF)] | 5.0 g |

Comparative Example 9

An inkjet ink of Comparative Example 9 was obtained in the same way as in Example 10 except that the polymer of the present invention (graft copolymer 2) used in Example 10 was changed to a commercially available pigment dispersant "SOLSPERSE 24000GR" (manufactured by Lubrizol Japan Ltd.).

Example 11 and Comparative Example 10

Inkjet inks of Example 11 and Comparative Example 10 were obtained in the same way as in Example 10 and Comparative Example 9, respectively, except that the pigment (b) used in Example 10 and Comparative Example 9 was changed to acetolone pigment (PY-120, Novoperm Yellow H2G, manufactured by Clariant(Japan)K.K.).

Example 12

An inkjet ink of Example 12 was obtained in the same way as in Example 10 except that the polymerizable compound (a), pigment (b), polymerization initiator (c) used in Example 10 were changed to following compounds.

| (b) Pigment [Dioxazine pigment PV-23, Hostaperm Violet BL] | 3.0 g |
|---|---|
| Polymer of the present invention [graft copolymer 2 obtained in the synthetic example]) | 0.9 g |
| (a) Polymerizable compound [propoxylated neopentyl glycol diacrylate] (NPGPODA, manufactured by Sartomer Company, Inc.) | 40.0 g |
| (a) Polymerizable compound [dipropylene glycol diacrylate (DPGDA, manufactured by DAICEL-CYTEC Company Ltd. | 50.6 g |
| (c) Polymerization initiator [acylphosphine oxide compound (LucirinTPO-L: manufactured by BASF] | 5.5 g |

Comparative Example 11

An inkjet ink of Comparative Example 11 was obtained in the same way as in Example 12 except that the polymer of the present invention (graft copolymer 2) used in Example 12 was changed to a commercially available pigment dispersant "SOLSPERSE 24000GR" (manufactured by Lubrizol Japan Ltd.).

(Evaluation of Ink Compositions)

The obtained inkjet inks were evaluated according to the following methods. The results are shown in Table 1.

—Viscosity—

The viscosity of each inkjet ink at 40° C. was measured with an E-type viscometer.

A: 30 mPa·s or less.

B: exceeding 30 mPa·s and less than 100 mPa·s.

C: 100 mPa·s or more (practically problematic level with regard to jetting ability).

—Stability—

The state of dispersion of each inkjet ink after being stored at 25° C. for one month and after being stored at 60° C. for 24 hours was evaluated visually and according to viscosity change.

A: No precipitate is generated, and an increase in viscosity is not observed.

B: No precipitate is generated, and although a slight increase in viscosity is observed, it is a non-problematic level with regard to jetting ability.

C: No precipitate is generated, but an increase in viscosity is observed, which is a practically problematic.

D: Precipitates are generated.

—Average Particle Diameter—

The volumetric average particle diameter D50 of each inkjet ink was measured using a light-scattering diffraction type particle size distribution measuring device (LA910, manufactured by Horiba, Ltd.) to carry out evaluation.

A: D50 is less than 100 nm.

B: D50 is 100 nm or more and less than 200 nm.

C: D50 is 200 nm or more.

—Curability—

The obtained ink compositions were applied to art paper by printing using an inkjet printer (printing density: 300 dpi, dotting frequency: 4 kHz, number of nozzles: 64) and then exposed to light by using a Deep UV lamp (SP-7, manufactured by Ushio Inc.) under an energy condition of 100 mJ/cm$^2$ to obtain a print sample.

A cured coating film was touched with fingers to evaluate the presence of a sticky feel according to the following standard.

TABLE 1

| | Pigment dispersant | Evaluation of ink composition | | | | |
|---|---|---|---|---|---|---|
| | | Viscosity | Stability (Room temperature) | Stability (60° C.) | Particle diameter | Curability |
| Example 1 | Polymer 1 | A | A | A | A | A |
| Example 2 | Polymer 2 | A | A | A | A | A |
| Example 3 | Polymer 3 | A | A | A | A | A |
| Example 4 | Polymer 4 | A | A | A | A | A |
| Example 5 | Polymer 5 | A | A | A | A | A |
| Example 6 | Polymer 6 | A | A | B | A | A |
| Comparative Example 1 | Commercially available dispersant 24000GR | A | C | C | A | A |
| Comparative Example 2 | Commercially available dispersant 32000 | A | A | C | A | A |
| Example 7 | Polymer 2 | A | A | A | A | A |
| Comparative Example 3 | Commercially available dispersant 24000GR | C | C | D | C | A |
| Comparative Example 4 | Commercially available dispersant 32000 | B | C | C | B | A |
| Example 8 | Polymer 2 | A | A | A | A | A |
| Comparative Example 5 | Commercially available dispersant 24000GR | A | C | C | B | A |
| Comparative Example 6 | Commercially available dispersant 32000 | A | B | C | B | A |
| Example 9 | Polymer 2 | A | A | A | A | A |
| Comparative Example 7 | Commercially available dispersant 24000GR | C | C | D | C | A |
| Comparative Example 8 | Commercially available dispersant 32000 | B | B | D | B | A |
| Example 10 | Polymer 2 | A | A | A | A | A |
| Comparative Example 9 | Commercially available dispersant 24000GR | B | C | D | B | A |
| Example 11 | Polymer 2 | A | B | B | A | A |
| Comparative Example 10 | Commercially available dispersant 24000GR | C | C | D | C | A |
| Example 12 | Polymer 2 | A | A | A | A | A |
| Comparative Example 11 | Commercially available dispersant 24000GR | C | C | D | A | A |

A: No sticky feel.
B: Slightly sticky.
C: Very Sticky.

As is clear from Table 1, the ink composition of the present invention was cured with high sensitivity when irradiated with a radiation ray, and it could therefore form a non-sticky high quality image. Even in the case where it was stored for a long time, the dispersibility and dispersion stability of the pigment were both satisfactory without any increase in viscosity associated with a reduction in the dispersibility of the pigment.

On the other hand, although the comparative examples using commercially available high molecular dispersant had favorable pigment dispersibility initially, they were deteriorated, particularly, in storage under a high-temperature condition (stability (60° C.)), showing that they had characteristics at a practically problematic level.

In the Examples described above, only data of Examples, in which polymers 1 to 6 were used as a pigment dispersant, are shown. However, it can be presumed that when the polymers of the present invention other than the polymers 1 to 6 are used as a pigment dispersant, they also have dispersion performance as the polymers 1 to 6 do. The reason for this is that the polymer of the present invention comprises, as a basic building block, a site interacting with a pigment, and a graft chain (macromonomer). Here, the site interacting with a pigment indicates the polymerizable compound of the present invention, and, according to necessity, also includes a basic monomer or acidic monomer (those which interact with acidic or basic site of the pigment surface). The graft chain (macromonomer) has a higher affinity for a dispersion medium than for a pigment and functions as a steric repulsive site that prevents the particles from aggregating in the dispersion liquid. Thus, it is necessary to select a graft chain depending on the dispersion medium.

The ink composition of the present invention can be suitably used in usual printing to form a sharp image with excellent coloring property, thus giving a high-quality printed material. The ink composition of the present invention can be suitably used also in the production of resists, color filters, and optical disks, and is useful also as an optical molding material.

In addition, since the application of the inkjet recording method makes it possible to form a high-quality image directly even on a non-absorptive recording medium based on digital data, the ink composition of the present invention can be suitably used also for the production of a printed material having a large area.

What is claimed is:

1. An ink composition comprising:
   a polymer;
   a polymerizable compound (a); and
   a pigment (b), wherein the polymer comprises a copolymer unit derived from a monomer represented by formula (1):

Formula (1)

wherein, in the formula (1), $R^1$ represents any one of a hydrogen atom, a substituted alkyl group, and an unsubstituted alkyl group; $R^2$ represents an alkylene group; W represents any one of —CO—, —C(=O)O—, —CONH—, —OC(=O)—, and an unsubstituted phenylene group; X represents any one of —CO—, —NHCO—, —OC(=O)—, —CH(OH)CH$_2$—, and —SO$_2$—; $R^3$ and $R^4$ each independently represents a monovalent substituent and the monovalent substituent is any one of a hydrogen atom, an alkyl group, an aryl group, a halogen atom, an alkoxy group, an aryloxy group, an alkylthio group, an arylthio group, an alkoxycarbonyl group, an acylamino group, a carbamoyl group, a cyano group, an alkylsulfonyl group, an arylsulfonyl group, an acyl group, a sulfamoyl group, an acyloxy group, a carboxyl group, and a sulfonyl group; $R^3$ and $R^4$ do not bind to each other to form a ring structure; and m and n each independently represent 0 or 1.

2. The ink composition according to claim 1, further comprising a polymerization initiator (c).

3. The ink composition according to claim 2, wherein the polymerizable compound (a) is a radical polymerizable compound, and the polymerization initiator (c) is a photo-radical generator.

4. The ink composition according to claim 2, wherein the polymerizable compound (a) is a cationic polymerizable compound, and the polymerization initiator (c) is a photo-acid generator.

5. The ink composition according to claim 1, wherein the polymer further comprises a copolymer unit derived from a monomer represented by formula (2):

Formula (1)

wherein, in the formula (2), $R^3$ and $R^4$ each independently represents a monovalent substituent and the monovalent substituent is any one of an alkyl group, an aryl group, a halogen atom, an alkoxy group, an aryloxy group, an alkylthio group, an arylthio group, an alkoxycarbonyl group, an acylamino group, a carbamoyl group, a cyano group, an alkylsulfonyl group, an arylsulfonyl group, an acyl group, a sulfamoyl group, an acyloxy group, a carboxyl group, and a sulfonyl group; and $R^3$ and $R^4$ do not bind to each other to form a ring structure.

6. The ink composition according to claim 1, wherein the polymer is a graft copolymer containing a copolymer unit derived from a macromonomer, wherein the macromonomer is a polymerizable oligomer having an ethylenically unsaturated double bond at a terminal thereof.

7. The ink composition according to claim 1, wherein the monomer represented by formula (1) is selected from the group consisting of the following compounds (M-1) to (M-12):

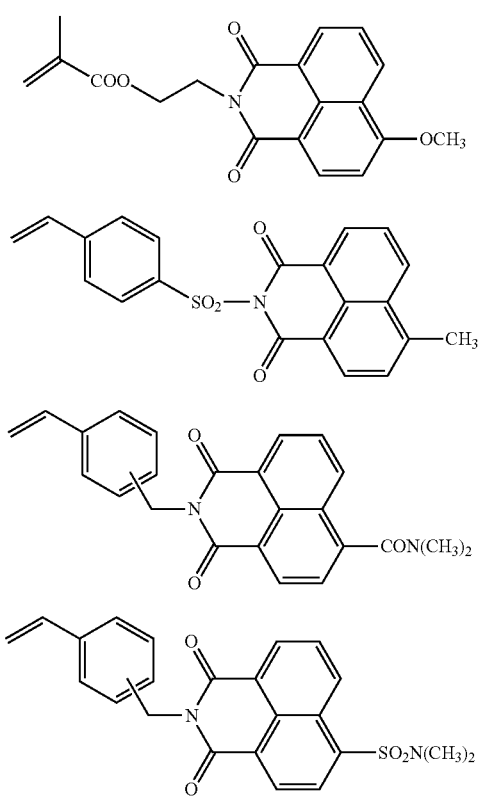

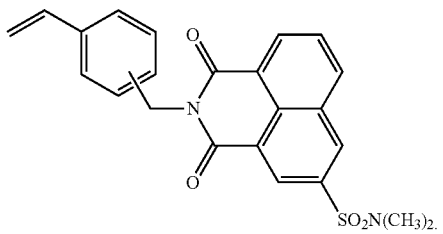

8. An inkjet recording method comprising:

ejecting an ink composition on a recording medium using an inkjet printer; and irradiating the ink composition ejected with an active radiation ray to cure the ink composition, wherein the ink composition comprises a polymer;

a polymerizable compound (a); and a pigment (b), wherein the polymer comprises a copolymer unit derived from a monomer represented by formula (1) as recited in claim 1.

* * * * *